US009526718B2

(12) United States Patent
Lee et al.

(10) Patent No.: US 9,526,718 B2
(45) Date of Patent: Dec. 27, 2016

(54) COMBINATION OF EFFECTIVE SUBSTANCES CAUSING SYNERGISTIC EFFECTS OF MULTIPLE TARGETING AND USE THEREOF

(75) Inventors: Doo Hyun Lee, Seoul (KR); Sunyoung Cho, Gyeonggi-do (KR)

(73) Assignee: VIVOZON, INC., Seoul (KR)

( * ) Notice: Subject to any disclaimer, the term of this patent is extended or adjusted under 35 U.S.C. 154(b) by 277 days.

(21) Appl. No.: 14/128,616

(22) PCT Filed: Jun. 28, 2012

(86) PCT No.: PCT/KR2012/005145
§ 371 (c)(1),
(2), (4) Date: Jan. 16, 2014

(87) PCT Pub. No.: WO2013/002584
PCT Pub. Date: Jan. 3, 2013

(65) Prior Publication Data
US 2015/0290181 A1   Oct. 15, 2015

(30) Foreign Application Priority Data

Jun. 28, 2011 (KR) ........................ 10-2011-0063289

(51) Int. Cl.
| | |
|---|---|
| A61K 36/00 | (2006.01) |
| A61K 31/445 | (2006.01) |
| A61Q 19/00 | (2006.01) |
| A61K 45/06 | (2006.01) |
| A61K 8/41 | (2006.01) |
| A61K 8/49 | (2006.01) |
| A61K 31/166 | (2006.01) |
| A61K 31/198 | (2006.01) |
| A61K 31/505 | (2006.01) |
| A61K 36/884 | (2006.01) |
| A61K 36/38 | (2006.01) |
| A61K 36/69 | (2006.01) |
| A61K 36/744 | (2006.01) |
| A61K 36/40 | (2006.01) |

(52) U.S. Cl.
CPC .............. *A61K 31/445* (2013.01); *A23L 33/10* (2016.08); *A61K 8/41* (2013.01); *A61K 8/4953* (2013.01); *A61K 31/166* (2013.01); *A61K 31/198* (2013.01); *A61K 31/505* (2013.01); *A61K 36/38* (2013.01); *A61K 36/40* (2013.01); *A61K 36/69* (2013.01); *A61K 36/744* (2013.01); *A61K 36/884* (2013.01); *A61K 45/06* (2013.01); *A61Q 19/00* (2013.01); *A61K 2800/10* (2013.01)

(58) Field of Classification Search
None
See application file for complete search history.

(56) References Cited

U.S. PATENT DOCUMENTS

| | | | |
|---|---|---|---|
| 2003/0235589 A1* | 12/2003 | Demopulos .......... | A61K 9/0019 424/178.1 |
| 2007/0123544 A1* | 5/2007 | Plourde et al. ............ | 514/261.1 |
| 2008/0242682 A1 | 10/2008 | Hirai et al. | |
| 2010/0311674 A1 | 12/2010 | Zhang | |
| 2011/0152205 A1* | 6/2011 | Liang .................. | A61K 31/352 514/23 |

FOREIGN PATENT DOCUMENTS

| | | | |
|---|---|---|---|
| CN | 101721589 A | * | 6/2010 |
| JP | 2005-526079 A | | 9/2005 |
| JP | 2008-531714 A | | 8/2008 |
| KR | 10-2007-0079497 A | | 7/2007 |
| KR | 10-2007-0085973 A | | 8/2007 |
| KR | 10-2009-0113462 A | | 2/2009 |
| KR | 10-2010-00091206 A | | 8/2010 |
| WO | 03077897 A1 | | 9/2003 |
| WO | 2006096434 A2 | | 9/2006 |

OTHER PUBLICATIONS

Houghton et al, a GlyT2 inhibitor, Org 25543, reduces mechanical allodynia in neuropathic rats. Society for Neuroscience Abstracts, (2001) vol. 27, No. 1, pp. 741.*
Baek, N., et al., "Effects of Several Medicinal Plants on the Activity of GABA-metabolizing Enzymes", "Kor. J. Pharmacogn.", 2000, pp. 23-27, vol. 31, No. 1.
Baik, E., et al., "Peripheral norepinephrine exacerbates neuritis-induced hyperalgesia", "Journal of Pain", 2003, pp. 212-221 (English Abstract), vol. 4, No. 4.
Cavadas, C., et al., "In vitro study on the interaction of *Valeriana officinalis* L. extracts and their amino acids on GABAA receptor in rat brain", "Arzneimittelforschung", Jul. 1995, pp. 753-755 (English Abstract), vol. 45, No. 7.
Chairungsrilerd, N., et al., "Gamma-mangostin, a novel type of 5-hydroxytryptamine 2A receptor antagonist", "Naunyn Schmiedebergs Arch Pharmacol", Jan. 1998, pp. 25-31 (English Abstract), vol. 357, No. 1.

(Continued)

*Primary Examiner* — Qiuwen Mi
(74) *Attorney, Agent, or Firm* — Hultquist, PLLC; Steven J. Hultquist

(57) ABSTRACT

Disclosed are a combination of active components inducing synergistic effects of multi-targeting and a use thereof. More particularly, disclosed are a functional food composition, a cosmetic composition, a pain-suppressive composition, and a composition for treatment or prevention of pruritus or atopic dermatitis, which comprise as active components, two or more components selected from a group consisting of (a) a 5-hydroxytryptamine subtype 2 (5-HT2) receptor antagonist; (b) a P2X receptor antagonist; and (c) any one of a glycine receptor agonist, a glycine transporter (GlyT) antagonist, a gamma-aminobutyric acid (GABA) receptor agonist, and a GABA transporter 1 (GAT1) antagonist.

4 Claims, 5 Drawing Sheets

(56) References Cited

OTHER PUBLICATIONS

Chaplan, S., et al., "Quantitative assessment of tactile allodynia in the rat paw", "Journal of Neuroscience Methods", 1994, pp. 55-63, vol. 53.
Cho, H., et al., "Inhibitory Effects of Extracts from Traditional Herbal Drugs on 5-Hydroxytryptamine Uptake in Primary Cultured Rat Brainstem Neurons", "Kor. J. Pharmacogn.", 1995, pp. 349-354, vol. 26, No. 4.
Choe, J., et al., "The Chemical Composition of Barley and Wheat Varieties", "J. Korean Soc. Food. Sci. Nutr.", Feb. 2005, pp. 223-229, vol. 34, No. 2.
Choi, J., et al., "Effects of Silk Fibroin Powder on Lipofuscin, Acetylcholine and Its Related Enzyme Activities in Brain of SD Rats", "Korean J. Seric. Sci.", 2000, pp. 120-125, vol. 42, No. 2.
Chueh, F., et al., "Hypotensive and Bradycardic Effects of dl-Tetrahydropalmatine Mediated by Decrease in Hypothalamic Serotonin Release in the Rat", "Jpn. J. Pharmacol.", 1995, pp. 177-180, vol. 69.
Chung, I., et al., "Behavioural pharmacology of polygalasaponins indicates potential antipsychotic efficacy", "Pharmacology, Biochemistry and Behavior", 2002, pp. 191-195, vol. 71.
Dixon, W., "Efficient Analysis of Experimental Observations", "Ann. Rev. Pharmacol. Toxicol.", 1980, pp. 441-462, vol. 20.
Huang, N., et al., "Gastrodia elata prevents rat pheochromocytoma cells from serum-deprived apoptosis: the role of the MAPK family", "Life Sciences", 2004, pp. 1649-1657, vol. 75.
Hwang, K., et al., "Screening of Inhibitory Activity of Edible Mushrooms on the Monoamine Oxidase", "Korean J. Food Sci. Technol.", 1997, pp. 156-160, vol. 29, No. 1.
Hwang, J., et al., "Survey for Amino Acid of Medicinal Herbs", "Korean Food Sci. Technol.", 1998, pp. 35-41, vol. 30, No. 1.
Hwang, K., et al., "Inhibitory Activity of the Fruit Extract of Gardenia jasminoides on Monoamine Oxidase", "Kor. J. Pharmacogn.", 2007, pp. 108-112, vol. 38, No. 2.
Imamura, T., et al., "An Extract (THC-002) of Ba-Wei-Die-Huang-Wan Inhibits Expression of Tachykinins, and P2X3 and TRPV1 Receptors, and Inhibits ATP-Induced Detrusor Overactivity in Spontaneously Hypertensive Rats", "Neurourology and Urodynamics", 2009, pp. 529-534, vol. 28.
Ito, Y., et al, "Pharmacological Effects of Hachi-mi-jio-gan Extract (Harncare) on the Contractle Response and on Pharmacologically Relevant Receptors in the Rat Bladder", "Yakugaku Zasshi", May 14, 2009, pp. 957-964, vol. 129, No. 8.
Jung, J., et al., "The Anxiolytic-like Effects of Scutellaria baicalensis Using Elevated Plus-Maze in Rats", "Kor. J. Pharmacogn.", 2004, pp. 22-27, vol. 35, No. 1.
Kim, S., et al., "An experimental model for peripheral neuropathy produced by segmental spinal nerve ligation in the rat", "Pain", Sep. 1992, pp. 355-363 (Abstract), vol. 50, No. 3.
Kim, M., et al., "Functional and Chemical Composition of Hwanggumkong, Yakong, and Huktae", "Korean J. Food Cookery Sci.", Dec. 2005, pp. 844-850, vol. 21, No. 6.
Kim, W., et al., "Anxiolytic-like effects of extracts from Albizzia julibrissin bark in the elevated plus-maze in rats", "Life Sciences", 2004, pp. 2787-2795, vol. 75.
Lee, J., et al., "Comparison of Nelumbinis Semen Extract with Hypericum Perforatum and Fluoxetine in Animal Model of Depression", "Korean J. Oriental Physiology and Pathology", 2006, pp. 830-843, vol. 20, No. 4.
Lee, K., et al., "Studies on Industrial Utilization of Silk Protein", "Kor. J. Food Sci. Ind.", 2003, pp. 25-37 (Only p. 1 Available), vol. 36, No. 3.
Moon, J., et al., "Nutrient Composition and Physicochemical Properties of Korean Taro Flours According to Cultivars", "Korean J. Food Sci. Technol.", Oct. 2010, pp. 613-619, vol. 42, No. 5.
Purves, D., et al., "GABA and Glycine", "Neuroscience 2nd Edition", 2001, p. 1, (accessed via http://www.ncbi.nlm.nih.gov/books/NBK11084), Publisher: Sinauer Associates, Published in: Sunderland, MA.
Xu, X., et al., "Protective Effects of Gastrodin on Hypoxia-Induced Toxicity in Primary Cultures of Rat Cortical Neurons", "Planta Med", Jun. 22, 2007, pp. 650-654, vol. 73.
Yu, H. et al., "Involvement of 5-HT1A and GABAA receptors in the anxiolytic-like effects of Cinnamomum cassia in mice", "Pharmacology, Biochemistry and Behavior", 2007, pp. 164-170, vol. 87.
Mingorance-Le Meur, A., et al., "Reversible inhibition of the glycine transporter GlyT2 circumvents acute toxicity while preserving efficacy in the treatment of pain", "British Journal of Pharmacology", Nov. 2013, pp. 1053-1063, vol. 170, No. 5.
Sang, M., et al, "Foundation review: A series of case studies: practical methodology for identifying antinociceptive multi-target drugs", "Drug Discovery Today", May 2012, pp. 425-434, vol. 17, No. 9/10.

\* cited by examiner

COMBINATION OF EFFECTIVE SUBSTANCES CAUSING SYNERGISTIC EFFECTS OF MULTIPLE TARGETING AND USE THEREOF

CROSS-REFERENCE TO RELATED APPLICATIONS

This application is a U.S. national phase under the provisions of 35 U.S.C. §371 of International Patent Application No. PCT/KR12/05145 filed Jun. 28, 2012, which in turn claims priority of Korean Patent Application No. 10-2011-0063289 filed Jun. 28, 2011. The disclosures of such international patent application and Korean priority patent application are hereby incorporated herein by reference in their respective entireties, for all purposes.

TECHNICAL FIELD

The present invention relates to a combination of active components inducing synergistic effects of multi-targeting and a use thereof, and more specifically, to a functional food composition, a cosmetic composition, a pain-suppressive composition, and a composition for treatment or prevention of pruritus or atopic dermatitis, which comprise as active components, two or more components selected from a group consisting of (a) a 5-hydroxytryptamine subtype 2 (5-HT2) receptor antagonist; (b) a P2X receptor antagonist; and (c) any one of a glycine receptor agonist, a glycine transporter (GlyT) antagonist, a gamma-aminobutyric acid (GABA) receptor agonist, and a GABA transporter 1 (GAT1) antagonist.

BACKGROUND ART

Conventionally, various diseases have been treated and prevented by using a "single target-single disease" approach to control a specific hormone or to target a single receptor. However, such an approach has not been sufficient to treat and prevent many diseases and may cause unexpected side effects.

For example, according to a current mechanism of action of antidepressants, symptoms of depression are reduced or relieved by increasing the amount of 5-HT as a neurotransmitter in a human body, and such an antidepressant has many serious side effects such as an increase in suicide rate, headache, diarrhea, melosalgia, a skin rash, palpitations, repetitive spasms, hyperhidrosis, edema, hypoactive sexual desire disorders, erectile dysfunction, and the like. Further, corticosteroids have been used to treat atopic dermatitis, but when discontinuing such a treatment, there may be a risk of rebound effects (dramatic worsening in a diseased part after discontinuing a medication). Therefore, nonsteroidal anti-inflammatory drugs or antihistamines that do not contain hormones such as corticosteroids have been used. However, such drugs have weak efficacy, and, thus, it is difficult to completely treat the diseases.

In order to solve these problems, as a suggestion for another direction of drug development, various studies into multi-target drugs have been carried out. However, at present, only combination drugs including two or three drugs have been used mostly for anticancer treatments, but there is limited knowledge about how to combine various targets.

Meanwhile, recently, in order to treat or prevent diseases, functional foods have been researched and produced in various forms such as functional foods or functional beverages with the purposes of vitality promotion, obesity prevention, improvement in atopic dermatitis, skin health, scalp health, pain control, refreshment, and the like. In addition to such functional foods, cosmetic compositions have been continuously researched and developed to achieve an aesthetic purpose, a therapeutic purpose, and a preventive purpose in the fields of skin whitening, antiwrinkle, skin elasticity, hair, and scalp. However, in most cases, by formulating various kinds of chemical components, efficacy corresponding to such components is given to cosmetics, or various kinds of formulations are created by creatively processing basic components. However, such formulations as described above also need a cosmetic composition having more various and higher efficacy and a toxicity problem still needs to be solved for safety in skin.

In view of the foregoing, recently, a lot of studies into natural substances having efficacy against diseases have been actively carried out. For example, Nelumbinis Semen extract has been used to treat depression; a method of producing seanol-based cream for pain treatment and anti-inflammation is known; salt, *Phyllostachys nigra* Munro extract, and the like have been provided to prevent and treat skin inflammations (Korean Patent Application Laid-open No. 10-2009-0113462); *Reynoutria elliptica* extract, *Sanguisorba officinalis* L. extract, *Coptis chinensis* extract, and the like have been provided to improve atopic dermatitis (Korean Patent Application Laid-open No. 10-2007-0079497); and a combination of *Glycyrrhiza uralensis* Fischer, green tea, *Asiasari radix* extract, and chitosan has been suggested to prevent periodontal diseases. Such natural substances can solve a toxicity problem of conventional compound-containing compositions and can be easily applied to functional foods, cosmetics, medicines, and the like. Therefore, natural substances have been recently applied to medicines, cosmetics, and functional foods in various ways.

Conventionally, however, it is general to produce a functional food composition based on descriptions of old documents or experience or to produce a composition based on a known-mechanism and apply the composition to a clinical test. There has not been a research study like the present invention on a specific combination of natural substances or compounds inducing synergistic effects based on a specific receptor-related mechanism.

Meanwhile, pain is a kind of warning system telling us that something is wrong in our body, and it is an essential symptom to maintain our normal life and can be typically classified into acute pain and chronic pain.

Although a lot of neuropathologic studies on pain have been actively carried out and various studies into treatments for pain have been carried out, even now, most treatments for pain depend on narcotic analgesics developed in the past.

A nervous system in charge of pain has a very complicated and parallel structure. A selective and potent drug on a single target may have lower efficacy than expected and is more likely to cause serious side effects. Therefore, there is a need for development of a multi-target drug capable of simultaneously controlling a pain signal process, or a central sensitization mechanism by adjusting multiple targets.

Pain relievers developed so far act on peripheral nerves or central nerves and relieve pain and can be typically classified into a nonsteroidal anti-inflammatory drug (NSAID), a COX-2 inhibitor, an opiate, a morphinomimetic, and flupirtine. It is reported that these pain relievers have many side effects and an addiction problem.

Accordingly, there is a significant need to develop novel medicaments capable of solving different side effects and the addiction problem of conventional pain relievers as well as relieving symptoms specific to pains.

Although a molecular-biological mechanism of pain and functions of drug targets based on the above mechanism have been relatively clearly disclosed, there is still considerable lack of understanding about a mechanism which results in pruritus (itching). However, since a significantly similar aspect is expressed between mechanisms respectively, in charge of pain and itching in peripheral tissues and spinal cords, the established mechanism and treatments for pain have also been applied to itching.

There is a complicated interaction between pain and itching. Usually, we strongly scratch an itchy spot to remove itching and this nociceptive stimulus suppresses itching, or an opioid analgesic causes itching. Such an antagonistic interaction is known. In addition, it has been discovered that the mechanisms in charge of pain and itching (central/peripheral sensitization, sense of difference, hypersensitization, etc.) significantly coincides with neuromodulators (NGF (nerve growth factor), TRPV1 (transient receptor potential vanilloid receptor 1), PARs (protease-activated receptors), etc.) as mediators thereof, which has been applied to treatments. By using a close relationship between peripheral mechanisms of two senses, a medicine, such as anti-NGF, having analgesic efficacy and anti-inflammatory efficacy has been developed, and gabapentin wiedly used as a medicine for neuropathic pain has been successfully applied to a medicine for chronic itching.

Causes of atopic dermatitis are not clear, and it has been reported that genetic factors, environmental factors, and immunologic factors are involved in atopic dermatitis. Currently-used medicines for atopic dermatitis mainly relieve symptoms, and, thus, there is an urgent requirement to develop a fundamental and innovative medicine. Atopic dermatitis occurs with a cycle of itching-scratching-further itching in which if one cannot treat or endure early itching and scratching an itchy spot, itching is worsened. As a result, in addition to pruritus (localized or systemic itching), other symptoms, such as rashes, chronic relapses, etc., of atopic dermatitis occur. Therefore, atopic dermatitis can be treated fundamentally by developing a drug capable of suppressing and treating early itching and preventing skin damage or an inflammatory response after scratches.

Based on such studies, the present inventors have made all possible efforts to supply a composite composition whose efficacy can be amplified by synergistic effects between components even if a small amount of the composite composition is used and a pharmaceutical composition having antipruritic efficacy and atopic dermatitis treatment efficacy as well as analgesic efficacy obtained by synergistic effects between drugs by using a multi-targeting mechanism. As a result, the present inventors have found that when substances acting on three targets with established synergistic effects are combined (particularly, natural substances functioning as agonists or antagonists of such receptors are appropriately combined), synergistic effects of multi-targeting bring about an increase in efficacy including pain control, relief of skin diseases such as pruritus and atopic dermatitis, prevention or improvement of depression, refreshment, wrinkle improvement, skin whitening, prevention or improvement of athlete's foot, hair growth promotion, etc. and completed the present invention.

The information as described in the above background art is only provided to improve understanding of a background technology of the present invention, however, other information with respect to prior art well known to persons having ordinary skill in the art to which the present invention pertains, may not be included therein.

DISCLOSURE

Technical Problem

An object of the present invention is to provide a combination of active components inducing synergistic effects of multi-targeting and a use thereof.

Another object of the present invention is to provide a functional food composition containing a combination of components acting on various receptors as an active component.

Another object of the present invention is to provide a cosmetic composition containing a combination of components acting on various receptors as an active component.

Another object of the present invention is to provide a composition for treatment or prevention for pain control, pruritus or atopic dermatitis, the composition containing a combination of components acting on various receptors as an active component.

Technical Solution

In order to accomplish the above objects, the present invention generally provides a combination of active components inducing synergistic effects of multi-targeting and a use thereof.

Specifically, the present invention generally provides a functional food composition, a cosmetic composition, a pain-suppressive composition and a composition for treatment or prevention of pruritus or atopic dermatitis comprising, as active components, two or more components selected from a group consisting of (a) a 5-hydroxytryptamine subtype 2 (5-HT2) receptor antagonist; (b) a P2X receptor antagonist; and (c) any one of a glycine receptor agonist, a glycine transporter (GlyT) antagonist, a gamma-aminobutyric acid (GABA) receptor agonist, and a GABA transporter 1 (GAT1) antagonist.

In addition, the present invention provides a functional food composition, a cosmetic composition, a pain-suppressive composition, and a composition for treatment or prevention of pruritus or atopic dermatitis comprising, as active components, one or more components selected from a group consisting of: (1) an antagonist simultaneously acting on a 5-HT2 (5-hydroxytryptamine subtype 2) receptor and a P2X receptor; (2) a 5-HT2 (5-hydroxytryptamine subtype 2) receptor antagonist, simultaneously acting as a glycine receptor agonist; (3) an antagonist simultaneously acting on a 5-HT2 (5-hydroxytryptamine subtype 2) receptor and a GlyT (Glycine Transporter); (4) a 5-HT2 (5-hydroxytryptamine subtype 2) receptor antagonist, simultaneously acting as a GABA (gamma-aminobutyric acid) receptor agonist; (5) an antagonist simultaneously acting on a 5-HT2 (5-hydroxytryptamine subtype 2) receptor and a GAT1 (GABA transporter 1); (6) a P2X receptor antagonist simultaneously acting as a glycine receptor agonist; (7) an antagonist simultaneously acting on a P2X receptor and a GlyT (Glycine Transporter); (8) a P2X receptor antagonist simultaneously acting as a GABA (gamma-aminobutyric acid) receptor agonist; (9) an antagonist simultaneously acting on a P2X receptor and a GAT1 (GABA transporter 1); (10) an antagonist simultaneously acting on a 5-HT2 (5-hydroxytryptamine subtype 2) receptor and a P2X receptor, and simultaneously acting as a glycine receptor agonist; (11) an antagonist simultaneously acting on a 5-HT2 (5-hydroxytryptamine subtype 2) receptor, a P2X receptor, and GlyT (Glycine Transporter); (12) an antagonist simultaneously acting on a 5-HT2 (5-hydroxytryptamine subtype 2) receptor and a P2X receptor, and simultaneously acting as a GABA (gamma-aminobutyric acid) receptor agonist; and (13) an antagonist simultaneously acting on a 5-HT2 (5-hydroxytryptamine subtype 2) receptor, a P2X receptor, and GAT1 (GABA transporter 1).

Advantageous Effects

According to a composite composition of the present invention, as compared with a case that components are treated respectively, when components are treated in a combination thereof, synergistic effects of multi-targeting bring about an increase in efficacy of all biological effects, in which mechanisms targeted by respective components are involved, such as pain control, relief of skin diseases such as pruritus and atopic dermatitis, prevention or improvement of depression, refreshment, pore minimization, wrinkle improvement, skin regeneration, skin health, recovery of skin condition, skin whitening, prevention or improvement of athlete's foot, recovery of scalp health and regeneration of scalp, hair growth promotion, prevention of gray hair, improvement of dental and periodontal diseases, etc.

BEST MODE

Figure 1:
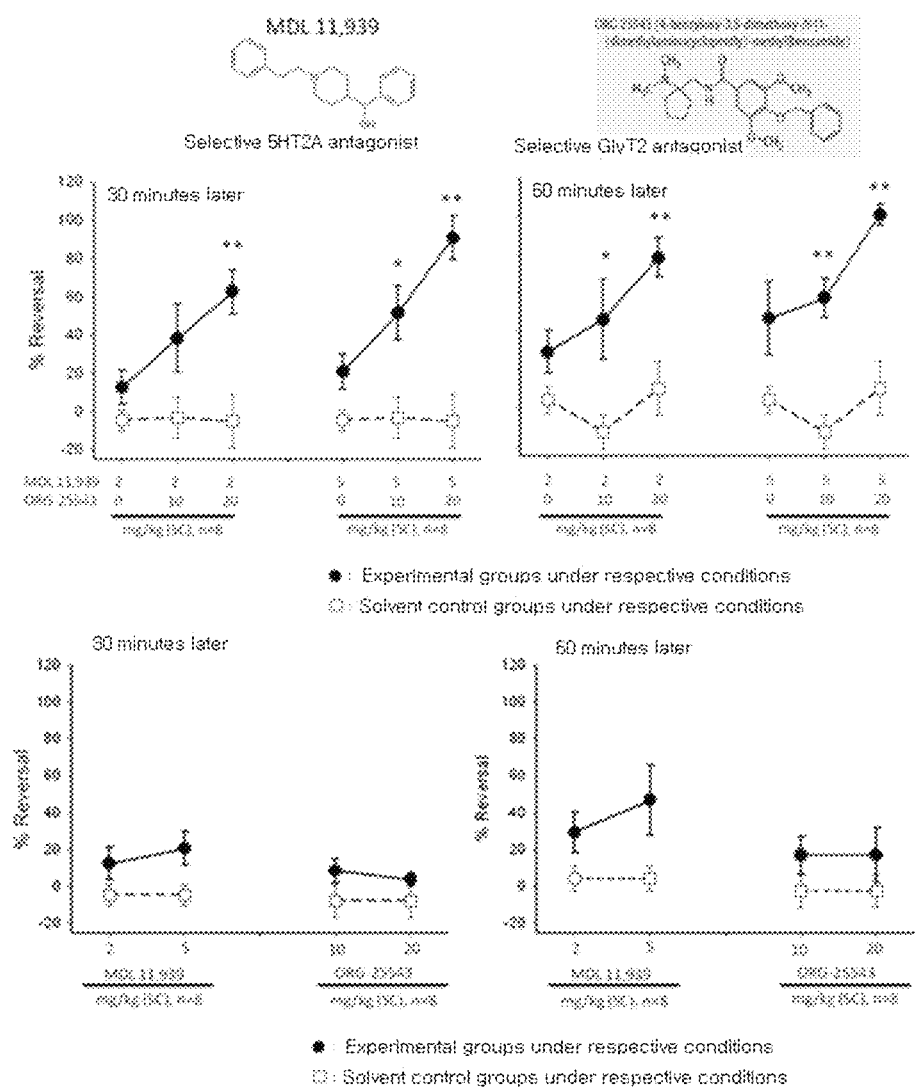
FIG. 1 shows an effect caused by respective treatments with MDL 11,939 as a selective antagonist of 5HT2A and ORG-25543 as a selective antagonist of GlyT2 and a synergistic effect on pain control caused by a combined treatment with the two drugs on a neuropathic pain rat model (SNL) (each group n=8).

All technical and scientific terminologies used in the present text have the same meanings as commonly understood by those skilled in the art to which the present invention pertains, until further defined. In general, nomenclature guidelines used in the present invention are well known and commonly used in the art.

Major terms used in the detailed description of the present invention may include as follows.

In the present invention, the term "component" or "active component" may be (a) a compound defined by a specific formula, natural extract, or a marker component, (b) extract derived from a natural substance whose chemical properties are not revealed, (c) protein or peptide, or (d) an antibody, and exhibits activity of an antagonist or an agonist to each receptor.

In the present invention, the term "combination of components" or "combination of active components" means a combination expressing synergistic effects in mechanisms, in which receptors targeted by respective components are involved, by combinations of (i) a compound defined by a specific formula or whose chemical properties are revealed, natural extract or an active component in a natural extract, or a marker compound, (ii) extract derived from a natural substance whose chemical properties are not revealed, (iii) protein, peptide, an antibody, or an antagonist or an agonist of each receptor. Such a combination includes various kinds of combinations including; a simple combination through a chemical and physical bonding reaction, a composite newly obtained by using various linkers or by chemical conversion.

In the present invention, the extract derived from the natural substance can be obtained by typical extraction methods including, but not limited to: cold extraction, hot extraction, boiling water extraction, etc. as traditionally descended from the past or as described in oriental medicine books; ultrasonication extraction, supercritical fluid extraction methods, etc. as described in textbooks; an extraction method of water or alcohol extract with an organic solvent such as hexane, chloroform, ethylacetate, butanol, etc.; or an extraction method for extracting a target component including a Stas-Otto extraction method for extracting alkaloid components and a steam distillation method for extracting essential oil.

In the present invention, the term "simultaneously act" means that a component of the present invention commonly acts on multiple receptors and exhibits activity of an antagonist or agonist.

In the present invention, the term "targeting multiple receptors (multi-targeting)" means simultaneously acting on receptors such as 5HT2A, P2X3, GlyT2, etc. and inducing synergistic effects. Thus, acting on multiple receptors as an antagonist or an agonist increases efficacy due to interactions and reduces an amount (that is, dosage) of a composition, resulting in a decrease in side effects. Such a multi-targeting mechanism can be applied to a composite of natural substances. The composite of natural substances may not have high efficacy as a single herb medicine. However, if it is used as a combined formulation, the composite of natural substances may have efficacy for improvement of diseases or functions with reduced side effects.

'Pain' used herein may include acute pain, chronic pain, inflammatory pain, neuropathic pain and migraine pain, as well as nociceptive pain or neuropathic pain. A disease or condition requiring a composition of the present invention may include, but not be limited to, pains associated with trauma, traumatic amputation, neuralgia, fibromyalgia, burn, abrasion (scratches), infection, laceration, cutting, etc., and pains arising due to diabetes, shingles, AIDS, chemotherapy for cancer patients, etc.

'Pruritus' used herein may include systemic or local pruritus and causes thereof may include, but not be limited to, diabetes, biliary atresia, liver disease with jaundice, nephritis, renal disease with chronic renal failure, leukemia, hyperthyroidism, hypothyroidism, iron-deficiency anemia, autoimmune disease such as lupus (systemic lupus erythematodes), cancerous disease such as Hodgkin's disease or multiple myeloma, menopausal disorder, AIDS, parasite disease, psychogenic disorder, neurogenic dermatitis, otitis externa, allergic dermatitis, atopic dermatitis, or the like.

'Atopic dermatitis' used herein may be derived from genetic causes, express symptoms such as eczema, dry skin, and have features of chronic pruritus.

In the present invention, the terms "skin health" and "recovery of skin condition" include skin moisturizing, blood circulation promotion, anti-microbial activity, removal of acne, live spots and freckles, removal of papules, pustules, and fine wrinkles around eyes, treatment of allergic skin diseases, skin whitening, skin regeneration, prevention or improvement of scars, improvement of skin elasticity, and prevention or improvement of aging skin.

Hereinafter, the present invention will be explained in detail.

According to an aspect of the present invention, there is provided a functional food composition comprising, as active components, two or more components selected from a group consisting of (a) a 5-hydroxytryptamine subtype 2 (5-HT2) receptor antagonist; (b) a P2X receptor antagonist; and (c) any one of a glycine receptor agonist, a glycine transporter (GlyT) antagonist, a gamma-aminobutyric acid (GABA) receptor agonist, and a GABA transporter 1 (GAT1) antagonist.

According to the functional food composition of the present invention, a combined antagonistic or activating function of the antagonist or agonist and synergistic effects for efficacy of natural substances bring about an increase in efficacy of all biological effects including; treatment or prevention of all diseases, in which mechanisms targeted by respective components are involved, for example, pain control, relief of skin diseases such as pruritus and atopic dermatitis, prevention or improvement of depression, refreshment, pore minimization, wrinkle improvement, skin regeneration, skin health, recovery of skin condition, skin whitening, prevention or improvement of athlete's foot, recovery of scalp health and regeneration of scalp, hair growth promotion, prevention of gray hair, improvement of dental and periodontal diseases, etc.; regeneration and recovery of metabolism, and the like.

According to another aspect of the present invention, there is provided a cosmetic composition comprising, as active components, two or more components selected from a group consisting of (a) a 5-hydroxytryptamine subtype 2 (5-HT2) receptor antagonist; (b) a P2X receptor antagonist; and (c) any one of a glycine receptor agonist, a glycine transporter (GlyT) antagonist, a gamma-aminobutyric acid (GABA) receptor agonist, and a GABA transporter 1 (GAT1) antagonist.

According to the cosmetic composition of the present invention, a combined antagonistic or activating function of the antagonist or agonist and synergistic effects for efficacy of natural substances bring about an increase in efficacy of all biological effects including; treatment or prevention of all diseases, in which mechanisms targeted by respective components are involved, for example, decrease of pain, relief of skin diseases such as pruritus and atopic dermatitis, prevention or improvement of depression, refreshment, pore minimization, wrinkle improvement, skin regeneration, skin health, recovery of skin condition, skin whitening, prevention or improvement of athlete's foot, recovery of scalp health and regeneration of scalp, hair growth promotion, prevention of gray hair, improvement of dental and periodontal diseases, etc.; regeneration and recovery of metabolism, and the like.

According to another aspect of the present invention, there is provided a composition for treatment or prevention comprising, as active components, two or more components selected from a group consisting of (a) a 5-hydroxytryptamine subtype 2 (5-HT2) receptor antagonist; (b) a P2X receptor antagonist; and (c) any one of a glycine receptor agonist, a glycine transporter (GlyT) antagonist, a gamma-aminobutyric acid (GABA) receptor agonist, and a GABA transporter 1 (GAT1) antagonist.

According to the composition for treatment or prevention of the present invention, a combined antagonistic or activating function of the antagonist or agonist and synergistic effects for efficacy of natural substances including; treatment or prevention of all diseases, in which mechanisms targeted by respective components are involved, for example, decrease of pain, relief of skin diseases such as pruritus and atopic dermatitis, prevention or improvement of depression, refreshment, pore minimization, wrinkle improvement, skin regeneration, skin health, recovery of skin condition, skin whitening, prevention or improvement of athlete's foot, recovery of scalp health and regeneration of scalp, hair growth promotion, prevention of gray hair, improvement of dental and periodontal diseases, etc.; regeneration and recovery of metabolism, and the like. In particular, the composition for treatment or prevention may be a pain-suppressive composition. Further, the composition for treatment or prevention may be a composition for treatment or prevention of pruritus or atopic dermatitis.

In this case, the functional food composition, the cosmetic composition, and the composition for treatment or prevention of disease may further comprise any one or more components of the agonists or the antagonists described in the item (c).

According to another aspect of the present invention, an agonist or an antagonist simultaneously acting on two or more targets may be included. The present invention provides a functional food composition, a cosmetic composition, a pain-suppressive composition, and a composition for treatment or prevention of pruritus or atopic dermatitis comprising, as active components, one or more components selected from a group consisting of: (1) an antagonist simultaneously acting on a 5-HT2 (5-hydroxytryptamine subtype 2) receptor and a P2X receptor; (2) a 5-HT2 (5-hydroxytryptamine subtype 2) receptor antagonist, simultaneously acting as a glycine receptor agonist; (3) an antagonist simultaneously acting on a 5-HT2 (5-hydroxytryptamine subtype 2) receptor and a GlyT (Glycine Transporter); (4) a 5-HT2 (5-hydroxytryptamine subtype 2) receptor antagonist, simultaneously acting as a GABA (gamma-aminobutyric acid) receptor agonist; (5) an antagonist simultaneously acting on a 5-HT2 (5-hydroxytryptamine subtype 2) receptor and a GAT1 (GABA transporter 1); (6) a P2X receptor antagonist simultaneously acting as a glycine receptor agonist; (7) an antagonist simultaneously acting on a P2X receptor and a GlyT (Glycine Transporter); (8) a P2X receptor antagonist simultaneously acting as a GABA (gamma-aminobutyric acid) receptor agonist; (9) an antagonist simultaneously acting on a P2X receptor and a GAT1 (GABA transporter 1); (10) an antagonist simultaneously acting on a 5-HT2 (5-hydroxytryptamine subtype 2) receptor and a P2X receptor, and simultaneously acting as a glycine receptor agonist; (11) an antagonist simultaneously acting on a 5-HT2 (5-hydroxytryptamine subtype 2) receptor, a P2X receptor, and GlyT (Glycine Transporter); (12) an antagonist simultaneously acting on a 5-HT2 (5-hydroxytryptamine subtype 2) receptor and a P2X receptor, and simultaneously acting as a GABA (gamma-aminobutyric acid) receptor agonist; and (13) an antagonist simultaneously acting on a 5-HT2 (5-hydroxytryptamine subtype 2) receptor, a P2X receptor, and GAT1 (GABA transporter 1).

In the present invention, the agonist or the antagonist simultaneously acting on two or more targets may include, for example, Cinnamomum cassia Blume acting as an antagonist of 5HT ('5HT antagonist') and an agonist of GABA ('GABA agonist'), Gastrodia elata Blume acting as a 5HT antagonist and a GABA agonist, and Alisma orientale (Sam.) Juz. acting as a P2X3 antagonist and a glycine agonist.

In addition, the composition may further comprise one or more components selected from a group consisting of (a) a 5-hydroxytryptamine subtype 2 (5-HT2) receptor antagonist; (b) a P2X receptor antagonist; and (c) any one of a glycine receptor agonist, a glycine transporter (GlyT) antagonist, a gamma-aminobutyric acid (GABA) receptor agonist, and a GABA transporter 1 (GAT1) antagonist.

According to still another aspect of the present invention, by combining natural substances respectively acting on three targets with established synergistic effects, it is possible to provide a combination of active components or a composite of the natural substances having a synergistic effect of the multi-targeting mechanism.

In the present invention, 5-HT (5-hydroxytryptamine) is a serotonin receptor and exists in the central and peripheral nervous systems, and it is involved in controlling secretion of neurotransmitters such as glutamate, GABA, dopamine, epinephrine/norepinephrine, acetylcholine, corticotropin, oxytocin, prolactin, and substance P so as to affect biological and neurological processes such as bellicosity, anxiety, appetite, a cognitive ability, a learning ability, memory, regulation of body temperature, etc. In particular, 5-HT2 is classified into 5HT2A, 5HT2B, and 5HT2C, and 5-HT2A is contained in blood vessels, the central nervous system, the gastrointestinal system, platelets, smooth muscles, etc., and takes part in toxic symptoms, anxiety, appetite, a cognitive ability, imagination, a learning ability, memory, mood changes, regulation of body temperature, etc. Further, as for 5-HT2A, it is known that polymorphism of genes is involved in a pain reaction.

5HT2A is widely distributed in peripheral sensory neurons, and most of 5HT2A includes both a peptidergic neuron and a non-peptidergic neuron, is expressed at a nociceptive neuron, and responds to serotonin released by response to an invading stimulus or an inflammatory reaction. 5HT2A is also expressed at an end of a descending facilitatory projection neuron in the midbrain, which relates to amplification of a pain signal of a spinal cord dorsal horn cell.

An inhibition effect to a 5HT2A receptor is important for an antipsychotic drug having a wide-range pharmacological profile or an antidepressant. This is effective in relieving negative thoughts, anxiety, or depressive symptoms, suppressing pain, and reducing side effects. A serotonin receptor has a complicated function of maintaining a fine balance between an excitatory neurotransmitter and an inhibitory neurotransmitter throughout the brain and such a balance is controlled by another receptor. This fact means that an effect of a selectively potent drug may be limited and may cause a serious side effect.

Examples of compounds and natural substances acting as the 5-HT2 (5-hydroxytryptamine subtype 2) receptor antagonists are as follows.

TABLE 1

| | |
|---|---|
| Compounds acting as the 5-HT2(5-hydroxtryptamine subtype 2) receptor antagonists | Altanserin hydrochloride; Clozapine; 4F 4PP oxalate; Fananserin; Ketanserin tartrate; MDL 11,939; Melperone hydrochloride; Mesulergine hydrochloride; Nefazodone hydrochloride; PNU 96415E; R-96544 hydrochloride; Risperidone; Sarpogrelate hydrochloride; Spiperone hydrochloride; Ziprasidone hydrochloride; Zotepine; ORG 50081; ACP-103; LY 2624803; Lonasen (Blonanserin); Lu-31-130; TS-032; SLV 313; Olanzapine; Quetiapine; Risperidone; Ziprasidone; Aripiprazole; Asenapine; Amitriptyline; Clomipramine; Cyproheptadine; Eplivanserin; Etoperidone; Iloperidone; Ketanserin; Methysergide; Mianserin; Mirtazapine; Nefazodone; Pimavanserin; Pizotifen; Trazodone; ATC 0175 hydrochloride; LY 272015 hydrochloride; RS 127445 hydrochloride; SB 200646 hydrochloride; SB 204741; SB 206553 hydrochloride; SB 221284; SB 228357; SDZ SER 082 fumarate; Agomelatine; Asenapine; BZP; Tegaserod, Yohimbine; N-Desmethylclozapine; RS 102221 hydrochloride; SB 242084; Dimebolin; Eltoprazine; Fluoxetine; and Lisuride |
| Natural substances acting as the 5-HT2 (5-hydroxytryptamine subtype 2) receptor antagonists | Mangosteen; γ-Mangostin; psychollatine; *Psychotria umbellata*; *Uncaria rhynchophylla*; rhynchophylline; isorhynchophylline; corynoxeine; hirsutine; Parthenolide; *Uncaria sinensis (Oliv.)* Havil.; *Albizia julibrissin Durazz.*; *Gardenia jasminoides* J. Ellis; *Polygala tenuifolia* Willd.; *Oldenlandia diffusa* (Willd.) Roxb.; *Corydalis ternata* Nakai; *Valeriana fauriei* Briq.; *Zizyphus jujuba* Mill; *Bombyx mori* L.; *Gastrodia elata* Bl.; *Rubia akane* Nakai; *Citrus unshiu* Markovich; *Ganoderma lucidum* (Leyss. ex Fr.) Karst.; and *Nelumbo nucifera* Gaertner |

As a representative natural substance acting as the 5-HT2 receptor antagonists in the present invention is mangosteen. Mangosteen is an evergreen tree in the family Staphyleaceae, and the mangosteen fruit is a tropical fruit called "queen of fruit". It has originated from Malaysia and also grown in Indonesia, Taiwan, the Philippines, India, Sri Lanka, and the like. In the areas where mangosteens grow naturally, mangosteen bark has been used for a long time as folk medicine for treating diarrhea, dysentery, eczema, burns, fever, enteropathy, itching, skin diseases, and the like. Recently, there are attempts to develop mangosteen bark extract as the raw material for a medicated soap and anti-aging cosmetics. This is because mangosteen extract is rich in various antioxidative components and it is easy to handle.

Mangosteen contains 40 or more kinds of xanthones most of which are biological active components having various pharmacological actions. Of these, α-mangostin and γ-mangostin have been studied actively and data of an antioxidant effect, an antibacterial effect, an antiviral effect, an antiinflammatory effect, an antitumor effect, an anticancer effect, and the like have been accumulated. In addition to the xanthones, mangosteen contains components having an antioxidant effect and an antibacterial effect such as catechin, polyphenol, polysaccharide, etc., polysaccharides, minerals, and vitamins. Of these, γ-mangostin has an antagonistic effect with respect to a 5-HT2A receptor, which has been proved in many documents (Chairungsrilerd et. al, γ-Mangostin, a novel type of 5-hydroxytryptamine 2A receptor antagonist, Naunyn-Schmiedebergs Archives of Pharmacology, 357: 25-31, 1998).

*Uncaria sinensis* (Oliv.) Havil. is the thorny green branch of *Uncaria sinensis* (Oli.) Havil or other closely related congeneric plants (family Rubiaceae), and it is also called "*Uncaria sinensis*" or "*Uncaria rhynchophylla* (MIQ.) JACKS". It has originated from China, and in Korea, it is also grown as a medicine in Youngcheon, North Gyeonsang Province. *Uncaria sinensis* (Oliv.) Havil. suppresses central nerves, lowers blood pressure, and expands peripheral blood vessels, and it is recorded in Dongui Bogam as a medicine for treating hypertension, headache, and the like. *Uncaria sinensis* (Oliv.) Havil. contains aquamigine, 3alpha-dihydrocardamine, cardamine, corynantheine, corynoxeine, hirsutheine, hirsutine, isocorynoxeine, iso mithraphyllic acid, isovaleric acid cotamine, mithraphyllic acid beta D glucophyranosyl ester, rhynophylline, strictosidine, vincoside, etc. as main components. It is reported that *Uncaria sinensis* (Oliv.) Havil. inhibits absorption of 5-HT in vitro (Hyun Mi Cho et. al, Inhibitory Effects of Extracts from Traditional Herbal drugs on 5-Hydroxytryptamine Uptake in Primary Cultured Rat Brainstem Neurons, Kor. J. Pharmacogn, 26(4):349-354, 1995).

*Albizia julibrissin* Durazz. is the bark of *Albizia julibrissin* and also called "*Albizia kalkora* (Roxb.) Prain" and "Albizziae Cortex". It is recorded in Dongui Bogam that *Albizia julibrissin* Durazz. has efficacy for pain control and physical and mental stability. Further, it is reported that *Albizia julibrissin* Durazz. functions as an antagonist of 5-HT2 (referred to as '5-HT2 antagonist') to exhibit an antianxiety effect (Won-Ki Kim et. al, Anxiolytic-like effects of extracts from *Albizzia julibrissin* bark in the elevated plus-maze in rats, Life Sciences, 75: 2787-2795, 2004).

*Gardenia jasminoides* J. Ellis is the fruit of *Gardenia jasminoides* Ellis or other closely related congeneric plants (family Rubiaceae). It has grown in Okinawa, Japan, Taiwan, and China and also grown in southern area of Korea. It is recorded in Dongui Bogam that this medicine is cold in nature and has diuretic and deintoxication effects. Main components of *Gardenia jasminoides* J. Ellis include crocin as a pigment, and genipin, genipiside, gardenoside as iridoid glucosides. Further, it is reported that *Gardenia jasminoides* J. Ellis extract has an inhibitory activity on a monoamine oxidase (MAO) which is an enzyme for controlling biosynthesis of serotonin (Hwang K. H., Park T. K., Inhibitory Activity of the Fruit Extract of *Gardenia jasminoides* on Monoamine Oxidase, Kor. J. Pharmacogn, 38:108-112, 2007).

*Polygala tenuifolia* Willd. is the root of *Polygala tenuifolia* Willdenow (family Polygalaceae) and it has been produced mainly in Manchuria, Mongolia, Amur, Usuri, Siberia, etc. *Polygala tenuifolia* Willd. contains polygalitol, tenuigenin, polygalasaponin, and xanthone derivatives. It is recorded in Dongui Bogam that this medicine has efficacies such as physical and mental stability, and improvement of forgetfulness, insomnia and skin diseases. It is reported that *Polygala tenuifolia* Willd. has an effect of inhibiting a 5-HT2 receptor through experiments. (Chung I W et al, Behavioural pharmacology of polygalasaponins indicates potential antipsychotic efficacy, Pharmacol Biochem Behav, 71:191-195, 2002). Further, it is reported that *Polygala tenuifolia* Willd. inhibits absorption of 5-HT in vitro (Hyun Mi Cho et. al, Inhibitory Effects of Extracts from Traditional Herbal drugs on 5-Hydroxytryptamine Uptake in Primary Cultured Rat Brainstem Neurons, Kor. J. Pharmacogn, 26(4):349-354, 1995).

*Oldenlandia diffusa* (Willd.) Roxb. is the whole grass of *Oldenlandia diffusa* (Willd.) Roxburgh (family Rubiaceae), and it has grown in Korea, China, Japan, Taiwan, Malaysia, India, etc. It is recorded in Ungok Bonchohak that *Oldenlandia diffusa* (Willd.) Roxb. has efficacy in deintoxication, antibacterial activity, and anti-inflammation.

*Corydalis ternata* Nakai is the tuber of *Corydalis ternate* Nakai or other closely related congeneric plants (family Papaveraceae). It is recorded in Dongui Bogam that *Corydalis ternata* Nakai has efficacy for pain control. *Corydalis ternata* Nakai contains corydaline, d1-tetrahydropalmatine, corybulmine, coptisine, 1-coryclamine, conadine, protopine, 1-tetrahydrocoptisine, d1-tetrahydrocoptisine, 1-isocorypalmine, dehydrocorydalmine, etc. Of these, it is found that d1-tetrahydropalmatine mediates inhibition of serotonin release (Chueh F Y et al, Hypotensive and bradycardic effects of d1-tetrahydropalmatine mediated by decrease in hypothalamic serotonin release in the rat, Jpn J Pharmacol, 69(2):177-80, 1995). Further, it is reported that *Corydalis ternata* Nakai inhibits absorption of 5-HT in vitro (Hyun Mi Cho et. al, Inhibitory Effects of Extracts from Traditional Herbal drugs on 5-Hydroxytryptamine Uptake in Primary Cultured Rat Brainstem Neurons, Kor. J. Pharmacogn, 26(4):349-354, 1995).

*Valeriana fauriei* Brig. is the root and rhizome of *Valeriana fauriei* Briquet or other closely related congeneric plants (family Valerianaceae) and also called "*Valeriana fauriei*". It has grown in Japan, China, and Taiwan. It is recorded in Ungok Bonchohak that *Valeriana fauriei* Brig. Has efficacy in pain control, physical and mental stability, and the like.

*Zizyphus jujuba* Mill is the seed of *Zizyphus jujuba* Miller (family Rhamnaceae). It has grown naturally in China, Mongolia, and mountainous areas, mostly dry places, throughout Korea. It is recorded in Dongui Bogam that *Zizyphus jujuba* Mill has efficacy for metal stability and is effective on insomnia. Main components of *Zizyphus jujuba* Mill include betuline, betulic acid, jujuboside, jojobogenin, sajoinine A-K, canaverine, methylasimilobine, Vit C, etc.

*Bombyx mori* L. is a cadaver of a *Bombyx mori* (Linne) (family Bombycidae) larva infected with *Beauveria bassiana* (Bals.) Vuill. and died from white muscardine. It has been raised in Japan, China, France, and Italy. It is recorded in Dongui Bogam that *Bombyx mori* L. has efficacy for deintoxication, headache, and the like. Further, it is reported that fibroin as a fibrous protein forming silk fiber of silkworm cocoon has an inhibitory activity on a monoamine oxidase (MAO) which is an enzyme for controlling biosynthesis of serotonin (J. H. Choi et al, Effects of Silk Fibroin Powder on Lipofuscin, Acetylcholine and Its Related Enzyme Activities in Brain of SD Rats, Korean J. Seric. Sci, 42(2): 20-125, 2000).

*Gastrodia elata* Bl. is the tuber of *Gastrodia elata* Blume (family Orchidaceae). It has grown in Korea, Japan, China, etc. It is recorded in Dongui Bogam that *Gastrodia elata* Bl. has efficacy for spasm, headache, and the like. *Gastrodia*

*elata* Bl. contains gastrodin as a main component and further contains vanillyl alcohol, 4-ethoxymethyl phenol, phydroxybenzyl alcohol, 3,4-dihydroxybenzaldehyde, and the like. It is published that p-hydroxybenzyl alcohol, vanillin, gastrodin, and the like as active components of *Gastrodia elata* Bl. act as serotonergic receptor antagonists and GABA agonists in connection with the central nervous system (Huang N K et al, Gastrodiaelata prevents rat pheochromocytoma cells from serum-deprived apoptosis: the role of the MAPK family, Life Sci. 75(13):1649-57, 2004), (Xu X et al, Protective effects of gastrodin on hypoxia-induced toxicity in primary cultures of rat cortical neurons, Planta Med, 73(7):650-4, 2007).

*Rubia akane* Nakai is the root of *Rubia akane* Nakai or other closely related congeneric plants (family Rubiaceae). It is recorded in Ungok Bonchohak that *Rubia akane* Nakai has efficacy for blood circulation and pain.

*Citrus unshiu* Markovich is the pericarp of the unripe fruit of *Citrus unshiu* Markovich or other closely related congeneric plants (family Rutaceae). It is recorded in Dongui Bogam that *Citrus unshiu* Markovich has efficacy for chest pain, mastitis, and the like. It is reported that *Citrus unshiu* Markovich inhibits absorption of 5-HT in vitro (Hyun Mi Cho et. al, Inhibitory Effects of Extracts from Traditional Herbal drugs on 5-Hydroxytryptamine Uptake in Primary Cultured Rat Brainstem Neurons, Kor. J. Pharmacogn, 26(4):349-354, 1995).

*Ganoderma lucidum* (Leyss. ex Fr.) Karst.) is the fruit body of *Ganoderma lucidum* Karsten or other closely related plants (family Polyporaceae). *Ganoderma lucidum* (Leyss. ex Fr.) Karst.) in the family *Ganoderma* has grown in the temperate zone or further north region of the northern hemisphere, including Korea, Japan, etc. It is recorded in Dongui Bogam that *Ganoderma lucidum* (Leyss. ex Fr.) Karst. has efficacy for physical and mental stability and improvement of forgetfulness, insomnia, and hypertension. Further, it is reported that *Ganoderma lucidum* (Leyss. ex Fr.) Karst. extract has an inhibitory activity on a monoamine oxidase (MAO) which is an enzyme for controlling biosynthesis of serotonin (Hwang K. H. et. al, Screening of Inhibitory Activity of Edible Mushrooms on the Monoamine Oxidase, Kor. J. Food sci. Technol, 29; 156-160, 1997).

*Nelumbo nucifera* Gaertner is the decoated seed of *Nelumbo nucifera* Gaertner (family Nymphaeaceae). Main components of *Nelumbo nucifera* Gaertner include anonaine, armepavine, asimilobine, liensinine, linalool, lirinidine, liriodenine, lotusine, phytol, pronuciferine, quercetin, and the like. It is recorded in Dongui Bogam that *Nelumbo nucifera* Gaertner is effective for physical and mental stability and improvement of insomnia. A stimulus of 5-HT can cause an increase in activity of MAPK. It is reported that *Nelumbo nucifera* Gaertner causes an increase in activity of MAPK so as to increase nervous stimulus (Lee Jin woo et al, Comparison of Nelumbinis Semen Extract with *Hypericum Perforatum* and Fluoxetine in Animal Model of Depression, Korean J. Oriental Physiology & Pathology, 20(4):830-843, 2006).

In the present invention, P2X receptors are cation-permeable ligand gated ion channels and can be classified into P2X3, P2X2/3, P2X2, and P2X7. It is known that the P2X receptors are bound to adenosine 5'-triphosphate (ATP) existing on their outside and involved in a change in heartbeat, nociception, and the like. Examples of compounds and natural substances acting as the P2X receptor antagonists are as follows.

TABLE 2

| | |
|---|---|
| Compounds acting as the P2X receptor antagonists | RO-3; NF 449; TNP-ATP triethylammonium; A 317491; RO-85; NF 110; NF 023; NF 279; NF 449; PPADS tetrasodium salt; Spinorpin; AF 219; AF 220, AF792; AZ 004; INS-48506; Evotec AG; A 438079 hydrochloride; A 740004; AZ 10606120 dihydrochloride; 5-BDBD; GW 791343 hydrochloride; KN 62; and Suramin |
| Natural substances acting as the P2X receptor antagonists | Palmijiwhang Pills; morroniside; loganin; Paeoniflorin; *Corni fructus*; *Alisma orientalis*; *Patrinia villosa* (Thunb.) Juss; *Strychnos nux-vomica*; *Menyanthes trifoliata* L.; *Lonicera japonica* Thunb.; *Paeonia lactiflora* Pall.; *Paeonia japonica* (Makino) Miyabe & Takeda; *Paeonia suffruticosa* Andr.; *Paeonia albiflora* Pallas var. *trichocarpa* Bunge; *Rubus crataegifolius* Bunge; *Ginkgo biloba* L.; *Rosa multiflora* Thunb.; *Rubus coreanus* Miq.; *Psoralea corylifolia* L.; *Psoralea corylifolia* L.; *Nelumbo nucifera* Gaertner; and *Lespedeza cuneata* G. Don |

As a representative natural substance acting as the P2X receptor antagonists is Palmijiwhang Pills. According to Tetsuya Imamura et al., Neurourology and Urodynamics, 28:529, 534, 2009, it is described that Palmijiwhang Pills acts on the P2X receptors. Main components of Palmijiwhang Pills include *Corni fructus* extract and *Alisma orientalis* extract.

*Corni fructus* is the fruit flesh, from which seeds are removed, of *Cornus officinalis* SIEB. et Zucc. as a deciduous tree in the family Cornaceae. Its main functional components include morroniside and loganin. Morroniside exists as a mixture of 7α-morroniside and 7β-morroniside and it is difficult to separate these components. Thus, it is general to perform measurement with loganin as a marker component of *Corni fructus*. It is recorded in Dongui Bogam that the above substance serves as a medicine for treating cold and painful waist and knees, and urinary incontinence. Further, it is reported that a composite herbal extract including *Corni fructus* reduces expression of the P2X receptors (Yakugaku Zasshi, Pharmacological effects of Hachi-mi-jio-gan extract (Harncare) on the contractile response and on pharmacologically relevant receptors in the rat bladder, the Pharmaceutical Society of Japan, August; 129 (8): 957-64, 2009.).

*Alisma orientalis* is a plant in the family Alismataceae and is an important herb medicine recorded in Shinnong Bonchokyung under alternative names and also recorded in the Korean Pharmacopoeia. *Alisma orientalis* has originated from *Alisma orientale* (Sam.) Juz. It is reported that main components of the corm of *Alisma orientalis* include alisols A and B, alisol A-monoacetate, alisol B-monoacetate, epialisol A, germacrenes C and D, etc., and the corm further contains essential oil, a small amount of alkaloid, asparagine, fatty acid, protein, and a great amount of starch (25%). It is recorded in Dongui Bogam that *Alisma orientalis* has efficacy for reducing fever and causing dieresis. Further, it is reported that a composite herbal extract including *Alisma orientalis* reduces expression of the P2X receptors (Yakugaku Zasshi, Pharmacological effects of Hachi-mi-jiogan extract (Harncare) on the contractile response and on pharmacologically relevant receptors in the rat bladder, the Pharmaceutical Society of Japan, August; 129 (8): 957-64, 2009.).

*Patrinia villosa* (Thunb.) Juss is also called as *Patrinia villosa* Jussieu or Whiteflower *Patrinia* and it is the root of *Patrinia villosa* Jussieu and *Patrinia scabiosaefolia* Fischer ex Link (family Valerianaceae). It is recorded in Dongui Bogam that *Patrinia villosa* (Thunb.) Juss has efficacy for pain control and deintoxication. Main components of

*Patrinia villosa* (Thunb.) Juss include villosol, villosolside, oleanolic acid, tetrapanax papyriferum saponin R-3, Loganin, and the like.

*Strychnos nux-vomica* is the ripe seed of *Strychnos nux-vomica* Linn (family Loganiaceae). It is recorded in Ungok Bonchohak that *Strychnos nux-vomica* has efficacy for arthritis and pain control. Main components of *Strychnos nux-vomica* include Strychnine, Loganin, Vomicine, Brucine, and the like.

*Menyanthes trifoliata* L. is a dicotyledonous perennial plant in the family Gentianaceae in the order Gentianales and also called a buckbean. It is recorded in Ungok Bonchohak that *Menyanthes trifoliata* L. has efficacy for physical and mental stability, and diuresis, treatment for gastritis and insomnia, and the like.

*Lonicera japonica* Thunb. is the stem and branch of *Lonicera japonica* Thunberg (family Caprifoliaceae). It is recorded in Dongui Bogam that *Lonicera japonica* Thunb. reduces a fever and has efficacy for skin itching.

*Paeonia lactiflora* Pall. is the root of a closely related congeneric plant (family Paeoniaceae). It is recorded in Dongui Bogam that *Paeonia lactiflora* Pall. Has efficacy in stopping pain. *Paeonia japonica* (Makino) Miyabe & Takeda. is colder in nature than *Paeonia lactiflora* Pall, thus having stronger efficacy for alleviation of fever. Main components of *Paeonia lactiflora* Pall. includes albiflorin, paeoniflorin, and the like.

*Paeonia suffruticosa* Andr. is the root bark of *Paeonia suffruticosa* Andrews (family Paeoniaceae). It is recorded in Dongui Bogam that *Paeonia suffruticosa* Andr. has efficacy for pain control and improvement of blood circulation. Main components of *Paeonia suffruticosa* Andr. include Paeoniflorin, Oxypaeoniflorin, Paeonol, Paeonoside, Paeonolide, Tannin, and the like. Further, it is reported that a composite herbal extract including *Paeonia suffruticosa* Andr. reduces expression of the P2X receptors (Yakugaku Zasshi, Pharmacological effects of Hachi-mi-jio-gan extract (Harncare) on the contractile response and on pharmacologically relevant receptors in the rat bladder, the Pharmaceutical Society of Japan, August; 129 (8): 957-64, 2009.).

*Rubus crataegifolius* Bunge is the unripe fruit of *Rubus crataegifolius* Bunge (family Rosaceae). It is recorded in Ungok Bonchohak that *Rubus* crataegifolius Bunge has efficacy for urine reduction and sterility.

*Ginkgo biloba* L. is the inner seed of the fruit of *Gingko biloba* Linne (family Ginkgoaceae). It is recorded in Dongui Bogam that *Ginkgo biloba* L. has efficacy for deinsectization, disinfection, and smoothing face and hands.

*Rosa multiflora* Thunb. is the root of *Rosa multiflora* Thunberg (family Rosaceae). It is recorded in Dongui Bogam as a medicine having efficacy for deinsectization and for treating various pains and bleeding.

*Rubus coreanus* Miq. is the root of *Rubus coreanus* Miq. It is recorded in Ungok Bonchohak as a medicine for treating pain and bleeding.

*Psoralea corylifolia* L. is the seed of *soralea corylifolia* Linne (family Leguminosae). It is also called by other names. It is recorded in Dongui Bogam that *Psoralea corylifolia* L. has efficacy for stopping diarrhea, recovering consciousness, and treating cold and painful waist and knees.

*Nelumbo nucifera* Gaertner is the stamen of *Nelumbo nucifera* Gaertner (family Nymphaceae). It is recorded in Dongui Bogam as a medicine for treating eczema and itching of skin.

*Lespedeza cuneata* G. Don is the aerial part of *Lespedeza cuneata* G. Don (family Leguminosae). It is recorded in Ungok Bonchohak as a medicine for treating edema, diarrhea, and all kinds of symptoms caused by external injuries.

In the present invention, it is known that a glycine receptor (GlyR) has a binding capacity to glycine as a neurotransmitter of amino acid, and is a representative inhibitory receptor in the central nervous system. Examples of compounds and natural substances acting as the glycine receptor agonists are as follows.

TABLE 3

| | |
|---|---|
| Compounds acting as the glycine receptor agonists | β-Alanine; D-alanine; L-alanine; hypotaurine; Glycine; D-cycloserine; DMG (Dimethylglycine); Sarcosine; Serine; and TMG (Trimethylglycine) |
| Natural substances acting as the glycine receptor agonists | Taurine; *Alisma orientalis* (Sam) Juzep; *Glycine max* (L.) Merr.; *Glycine max*; *Triticum aestivum* L.; *Dioscorea japonica* Thunb.; *Colocasia esculenta* (L.) Schott; Milacemide; *Zizyphus jujuba* Mill; *Bombyx mori* L.; and *Glycyrrhiza uralensis* Fisch |

*Alisma orientalis* (Sam) Juzep is the tuber, from which rootlets and periderm are removed, of *Alisma orientale* Juzepczuk or other closely related congeneric plants (family Alismataceae). It is recorded in Dongui Bogam that *Alisma orientalis* (Sam) Juzep has efficacy for reducing fever and causing dieresis. It is reported that *Alisma orientalis* (Sam) Juzep has a high content of glycine. (Hwang J B, Yang M O, Shin H K. 1998. Survey for amino acid of medicinal herbs. Korean J Food Sci Technol 30: 35-41.)

Legumes corresponding to the above mentioned *Glycine max* (L.) Merr. and *Glycine max* include Glycine Semen Germinatum (*Glycine max* Merr.), Glycinis Nigra Testa (*Glycine soja* S. et Z.), Glycinis Nigra Testa (*Glycine max* Merr.), Sojae Semen (*Glycine max* Merr.), Glycine Semen (*Glycine max* Merr.), Glycinis Nigrae Semen (*Glycine max* Merr.), Sojae Semen Praeparatum (*Glycine max* Merr.), Liquor Salsus ex Faba (*Glycine max* Merr.), Liquor Salsus ex Faba (*Glycine max* Merr.), Sojae Semen Praeparatum (*Glycine max* Merr.), Glycine Semen Fermentitum Insulsum (*Glycine max* Merr.) (Pharmacopoeia of People's Republic of China), fermented soybean lump (*Glycine max* Merr.). Herein, Glycine Semen *Germinatum* has efficacy for controlling a kidney and dispersing excessive dampness and fever; Glycinis Nigrae Semen has efficacy for deintoxication and diuresis; and Glycine Semen has efficacy for treating diabetes and preventing cancer. It is reported that the legumes have a high content of glycine (M. J. Kim, K. S. Kim, Functional and Chemical Composition of Hwanggumkong, Yakong and Huktae, Korean J. Food Coofery SCI. 2005, 21(6); 844-850).

Glycine Semen (*Glycine max*) is the fruit of *Glycine max* Merrill (family Leguminosae). It is recorded in Dongui Bogam as a medicine having efficacy for deintoxication and skin wounds.

*Triticum aestivum* L. is the seed of *Triticum aestivum* Linne (family Gramineae). It is recorded in Dongui Bogam as a medicine for stopping pain and treating localized swelling. Further, it is reported that wheat is higher in a content of glycine than other grains (J S Choe, J Y Youn, The Chemical Composition of Barley and Wheat Varieties, J. Korean soc Food Sci Nutr, 34(2):223-229, 2005).

*Dioscorea japonica* Thunb. is the rhizome (rhizophore) as dried naturally or in steamed and dried state, from which periderm is removed, of *Dioscorea batatas* Decaisne or *Dioscorea japonica* Thunberg (family Dioscoreaceae). It is recorded in Dongui Bogam as a medicine for treating lack of appetite and diarrhea. Main components of *Dioscorea japonica* Thunb. include saponin, mucin, arginine, allantoin, amylase, choline, and the like.

*Colocasia esculenta* (L.) Schott is the rhizome of *Colocasia esculenta* (L.) Schott (family Araceae). It is recorded in Dongui Bogam that *Colocasia esculenta* (L.) Schott has efficacy for deintoxication and antiinflammation. It is reported that *Colocasia esculenta* (L.) Schott has a high content of glycine among amino acids (J. H. Moon et al, Nutrient Composition and Physicochemical Properties of Korean Taro Flours According to Cultivars, Korean J Food Sci Technol, 42(5):613-619, 2010).

*Zizyphus jujuba* Mill is the seed of *Zizyphus jujuba* Miller (family Rhamnaceae). It has grown naturally in China, Mongolia, and mountainous areas, mostly dry places throughout Korea. It is recorded in Dongui Bogam that *Zizyphus jujuba* Mill has efficacy for mental stability and is effective on insomnia. Main components of *Zizyphus jujuba* Mill include betuline, betulic acid, jujuboside, jojobogenin, sajoinine A-K, canaverine, methylasimilobine, and Vit C, etc. It is reported that *Zizyphus jujuba* Mill has a high content of glycine (Hwang J B, Yang M O, Shin H K, Survey for amino acid of medicinal herbs, Korean J Food Sci Technol, 30: 35-41, 1998).

*Bombyx mori* L. is a cadaver of a *Bombyx mori* (Linne) (family Bombycidae) larva infected with *Beauveria bassiana* (Bals.) Vuill. and died from white muscardine. It has been raised in Japan, China, France, and Italy. It is recorded in Dongui Bogam that *Bombyx mori* L. has efficacy for deintoxication, headache, and the like. Further, it is reported that fibroin as a fibrous protein forming silk fiber of silkworm cocoon has a high content of glycine (Lee K G et al, Studies on industrial utilization of silk protein, Kor J Food Sci Ind, 36:25-37, 2003).

*Glycyrrhiza uralensis* Fisch is the root and rhizome of *Glycyrrhiza uralensis* Fischer, *Glycyrrhiza glabra* Linné or *Glycyrrhiza inflata* Batal. (family Leguminosae) from which periderm is removed or not. It is recorded in Dongui Bogam as a medicine for stopping pain and treating amnesia.

A GlyT (Glycine Transporter) exists in the brain, the spinal cord, and the brainstem and is classified into GlyT1 and GlyT2 depending on a position and a function. The GlyT maintains a concentration of glycine, which is an inhibitory neurotransmitter, in the synaptic cleft and induces hyperekplexia by abnormal activity. Examples of compounds and natural substances acting as the GlyT receptor antagonists are as follows.

TABLE 4

| Compounds acting as the GlyT (Glycine Transporter) receptor antagonists | LY 294002; ALX 5407; FPPSBPAA; Lu AA20465; Merck 7C; MTHMPNMglycine; ORG 24461; OEF 24598; ORG 25935; Sarcosine; SSR 504734; SSR 103800; CP 802079; ALX 1393; ALX 1405; Amoxapine; Emodin; ORG 25543; Propionylpromazine; Tyrphostin AG528; Amitrityline; Chlorpromazine; Clozapine; Doxepin; Haloperidol; Nortriptyline; Thioridazine; and LY 2365109 |
|---|---|
| Natural substances acting as the GlyT (Glycine Transporter) receptor antagonists | N-arachidonyl glycine, NAGly |

A GABA (γ-aminobutyric acid) receptor uses a γ-aminobutyric acid (GABA), which is a representative inhibitory neurotransmitter acting on the central nervous system, as a ligand and is classified into $GABA_A$ as a ligand gated ion channel and $GABA_B$ as a metabotropic receptor. Agonists of the GABA receptor are used as an antianxiety drug, a seizure-suppressant, and a stabilizer. It is known that some agonists have side effects of inducing anterograde amnesia and reterograde amnesia. Examples of compounds and natural substances acting as the GABA receptor agonists are as follows.

TABLE 5

| Compounds acting as the GABA receptor agonists | Gabapentin; (RS)-Baclofen; Pregabalin; Acamprosate Calcium; Allopregnanolone; rac BHFF; CGP 13501; CGP 7930; Ganaxolone; GS 39783; Indiplon; Isoguvacine hydrochloride; L-655708; L-838417; Muscimol; ORG 20599; ZAPA sulfate; THIP hydrochloride; TPMPA; U98943A; Valerenic acid; SKF 97541; TACA; TCS 1105; TCS 1205; Primidone; alcohol; barbiturate; benzodiazepine; carisoprodol; chloral hydrate; etomidate; glutethimide; L-theanine; KAVA; methaqualone; propofol; Baclofen; phenibut; Picamilon; GHB (-hydroxybutyric acid); and Tiababine |
|---|---|
| Natural substances acting as the GABA (gamma-aminobutyric acid) receptor agonists | Pregnanolone; *Valeriana fauriei* Briquet; *Zizyphus jujuba* Mill; *Scutellaria baicalensis* Georgi; *Cinnamomum cassia* Blume; and *Gastrodia elata* B1. |

*Valeriana fauriei* Briq. is the root and rhizome of *Valeriana fauriei* Briquet or other closely related congeneric plants (family Valerianaceae) and also called as *Valeriana fauriei*. It has grown in Japan, China, and Taiwan. It is recorded in Ungok Bonchohak that *Valeriana fauriei* Briq. has efficacy for pain control, physical and mental stability, and the like. It is reported that *Valeriana fauriei* Briq. has a sedative effect caused by a GABAergic mechanism (Cavadas C et al, In vitro study on the interaction of *Valeriana officinalis* L. extracts and their amino acids on GABAA receptor in rat brain, Arzneimittelforschung, 45:753-755, 1995).

*Zizyphus jujuba* Mill is the seed of *Zizyphus jujuba* Miller (family Rhamnaceae). It has grown naturally in China, Mongolia, and mountainous areas, mostly dry places, throughout Korea. It is recorded in Dongui Bogam that *Zizyphus jujuba* Mill has efficacy for mental stability and is effective on insomnia. Main components of *Zizyphus jujuba* Mill include betuline, betulic acid, jujuboside, jojobogenin, sajoinine A-K, canaverine, methylasimilobine, Vit C, etc. It is reported that *Zizyphus jujuba* Mill increases activity of glutamate dehydrogenase (GH) which is an enzyme related to biosynthesis of GABA (E. M. Ahn et al, Effects of Several Medicinal Plants on the Activity of GABA-metabolizing Enzymes, Kor. J. Pharmacogn, 31:23-27, 2000).

*Scutellaria baicalensis* Georgi is the root, from which periderm is removed, of *Scutellaria baicalensis* Georgi (family Labiatae). It is recorded in Dongui Bogam that *Scutellaria baicalensis* Georgi has efficacy for stability during pregnancy and hemostatis. Main components of *Scutellaria baicalensis* Georgi include baicalin, baicalein, woogonin, woogonoside, neobaicalein, β-sistosterol, and the like. Further, it is reported that *Scutellaria baicalensis* Georgi has an antianxiety effect via the $GABA_A$ nervous system (Jung. J. W. et al, The Anxiolytic-like Effects of *Scutellaria baicalensis* Using Elevated Plus-Maze in Rats, Kor. J. Pharmacogn, 35(1):22-27, 2004).

*Cinnamomum cassia* Blume is the bark of the tree trunk of *Cinnamomum cassia* Blume (family Lauraceae). It is recorded in Dongui Bogam as a medicine for treating cold and painful waist and knees and dull pain in uterus. Further, it is reported that *Cinnamomum cassia* Blume can act on the $GABA_A$ receptor to exhibit an antianxiety effect (Yu H S, Lee S Y, Jang C G, Involvement of 5-HT1A and GABAA receptors in the anxiolytic-like effects of *Cinnamomum cassia* in mice, Pharmacol Biochem Behav, May; 87(1): 164-70, 2007).

*Gastrodia elata* Bl. is the tuber of *Gastrodia elata* Blume (family Orchidaceae). It has grown in Korea, Japan, China, etc. It is recorded in Dongui Bogam that *Gastrodia elata* Bl. has efficacy for spasm, headache, and the like. *Gastrodia elata* Bl. has gastrodin as a main component and further contains vanillyl alcohol, 4-ethoxymethyl phenol, phydroxybenzyl alcohol, 3,4-dihydroxybenzaldehyde, and the like. It is published that p-hydroxybenzyl alcohol, vanillin, gastrodin, and the like, as active components of *Gastrodia elata* Bl., act as 5HT antagonists and/or GABA agonists in connection with the central nervous system (Huang N K et al, Gastrodiaelata prevents rat pheochromocytoma cells from serum-deprived apoptosis: the role of the MAPK family, Life Sci. 75(13):1649-57, 2004), (Xu X et al, Protective effects of gastrodin on hypoxia-induced toxicity in primary cultures of rat cortical neurons, Planta Med, 73(7): 650-4, 2007).

In addition to the agonists of the GABA receptor, GAT1 (GABA transporter 1) is a Na and Cl-dependent GABA transporter 1 and removes GABA from the synaptic cleft. Examples of compounds acting as the GAT1 receptor antagonists are as follows.

TABLE 6

| | |
|---|---|
| Compounds acting the GAT1 (GABA transporter 1) receptor antagonists | Vigabatrin; NNC711; (S)-SNAP5114; Alanine; CI966 hydrochloride; (±)-Nipecotic acid; NNC05-2090 hydrochloride; NNC711; Riluzole hydrochloride; SKF89976A hydrochloride; (S)-SNAP5114; and TACA |

Most of inhibitory neurons existing in the central nervous system (brain and spinal cord) simultaneously use glycine and GABA as neurotransmitters, and these two components has a similar function. (Purves D, Augustine G J, Fitzpatrick D, et al., editors. Neuroscience. 2nd edition. Sunderland (Mass.): Sinauer Associates; 2001. GABA and Glycine. Available from: http://www.ncbi.nlm.nih.gov/books/NBK11084/). Therefore, the glycine receptor agonists, the GlyT antagonists, the GABA receptor agonists, and the GAT1 antagonist are classified into the same group as having similar effects.

In an embodiment of the present invention, in order to identify synergistic effects on a 5-HT2A receptor and a GlyT2 receptor, pain animal models were treated with MDL 11,939 as a 5-HT2A antagonist and ORG2553 as a GlyT2 antagonist, respectively, or as a combination thereof. As a result, when the 5-HT2A antagonist or GlyT2 antagonist is used alone, no or very little pain relieving effect is expressed. On the other hand, it is demonstrated that pain relieving effect is remarkably improved by the combined treatment of the antagonists (FIG. 1).

Figure 2:
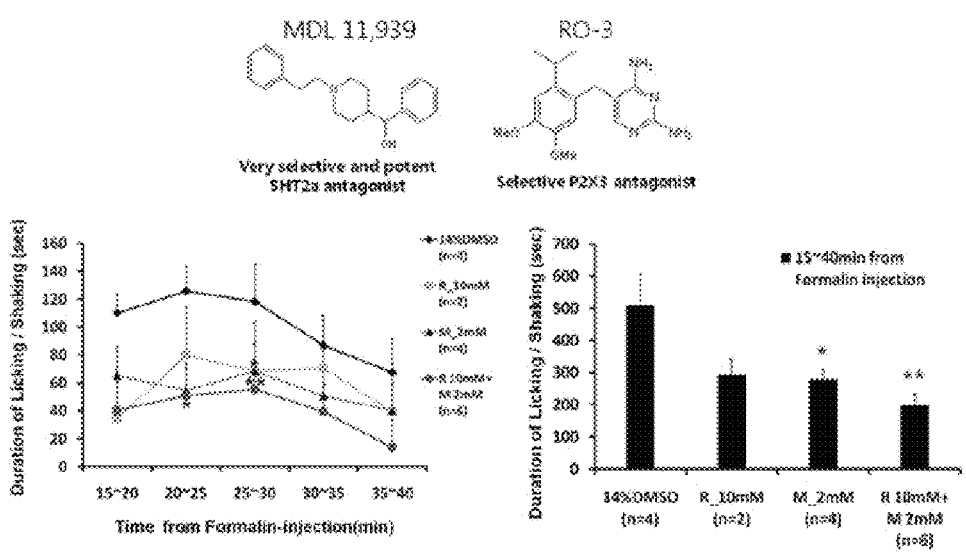
FIG. 2 provides graphs showing that, as compared with respective treatments using MDL 11,939 as a 5HT2A antagonist and RO-3 as a P2X3 antagonist given to a rat formalin model having pain caused by injection of formalin into its soles, a combined treatment with the two drugs increases efficacy for controlling the pain induced by formalin (each group n=2 to 6).

In another embodiment of the present invention, pain animal models were treated with MDL 11,939 as a 5-HT2A antagonist and RO-3 as a P2X3 antagonist, respectively, or as a combination thereof. As a result, it is demonstrated that pain relieving effect is largely improved by the combined treatment of the antagonists, as compared with the respective treatments (FIG. 2).

In another embodiment of the present invention, neuropathic pain animal models were treated with "mangosteen" extract as a natural substance acting as a 5-HT2 receptor antagonist, "Palmijiwhang Pills" as a natural substance acting as a P2X receptor antagonist, and "glycine" as a glycine receptor agonist in a combined manner. As a result, it is expressed that pain is remarkably relieved by synergistic effects of multi-targeting between the natural substances (FIG. 3a). On the other hand, when the mangosteen extract or the Palmijiwhang Pills is used alone, very little pain relieving effect is expressed (FIGS. 3b and 3c).

Figure 4:
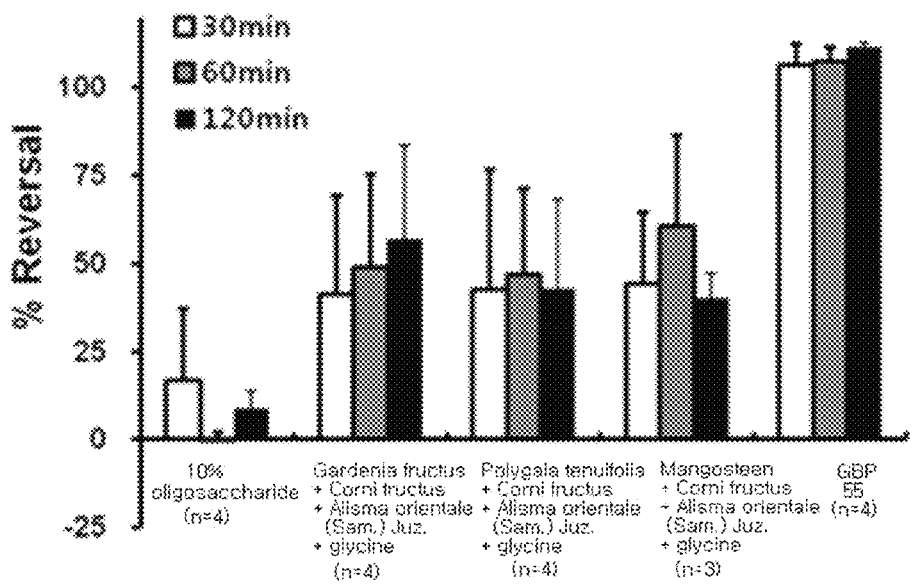
FIG. 4 shows a synergistic effect on pain control caused by a combined treatment with any one of "*gardeniae fructus*" extract, "*polygala tenuifolia*" extract, or "mangosteen" extract which are natural substances acting as a selective 5HT2A antagonist, "*Corni fructus* and *Alisma orientale* (Sam.) Juz." extracts as a P2X antagonist, and "glycine" as a glycine receptor agonist on a neuropathic pain rat model (SNL) (n=3 to 4). A result of each experiment was compared with a result of gabapentin (60 mpk, i.p.) as a positive control.

In another embodiment of the present invention, when neuropathic pain animal models were treated with "*gardeniae fructus*" extract, "*polygala tenuifolia*" extract, or "mangosteen" extract as a natural substance acting as a 5-HT2 antagonist, "*Corni fructus/Alisma orientale* (Sam.) Juz." extracts as a P2X receptor antagonist, and "glycine" as a glycine receptor agonist in a combined manner, it is demonstrated that pain is relieved by synergistic effects (FIG. 4). Thus, it can be seen that the composition for treatment or prevention in the present invention has pain relieving effects.

Figure 5:
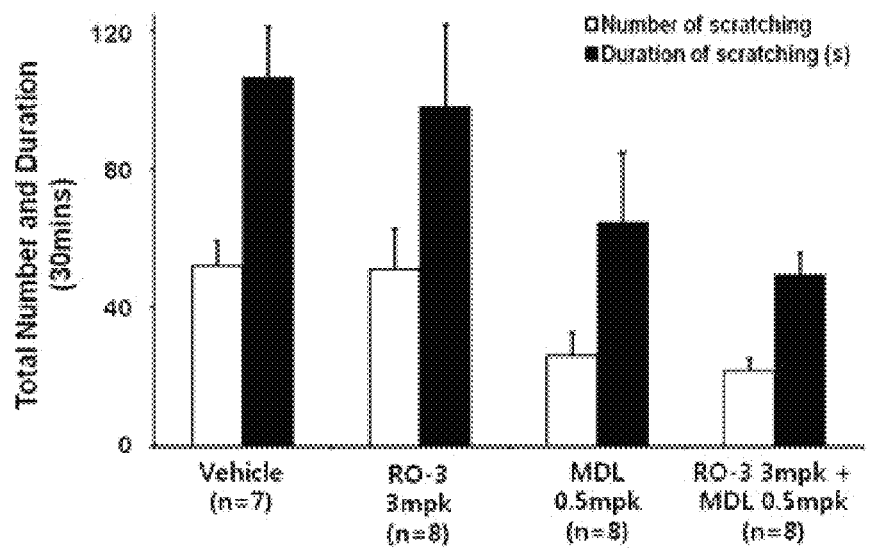
FIG. 5 shows that, as compared with respective treatments using MDL 11,939 as a 5HT2A antagonist and RO-3 as a P2X3 antagonist given to an itching rat model, a combined treatment with the two drugs remarkably decreases itching (n=7 to 8).

In another embodiment of the present invention, itching animal models were treated with MDL 11,939 as a 5-HT2A antagonist and RO-3 as a P2X3 antagonist, respectively, or as a combination thereof. As a result, it is demonstrated that pain relieving effect is increased by the combined treatment of the antagonists, as compared with the respective treatments (FIG. 5).

Figure 6:
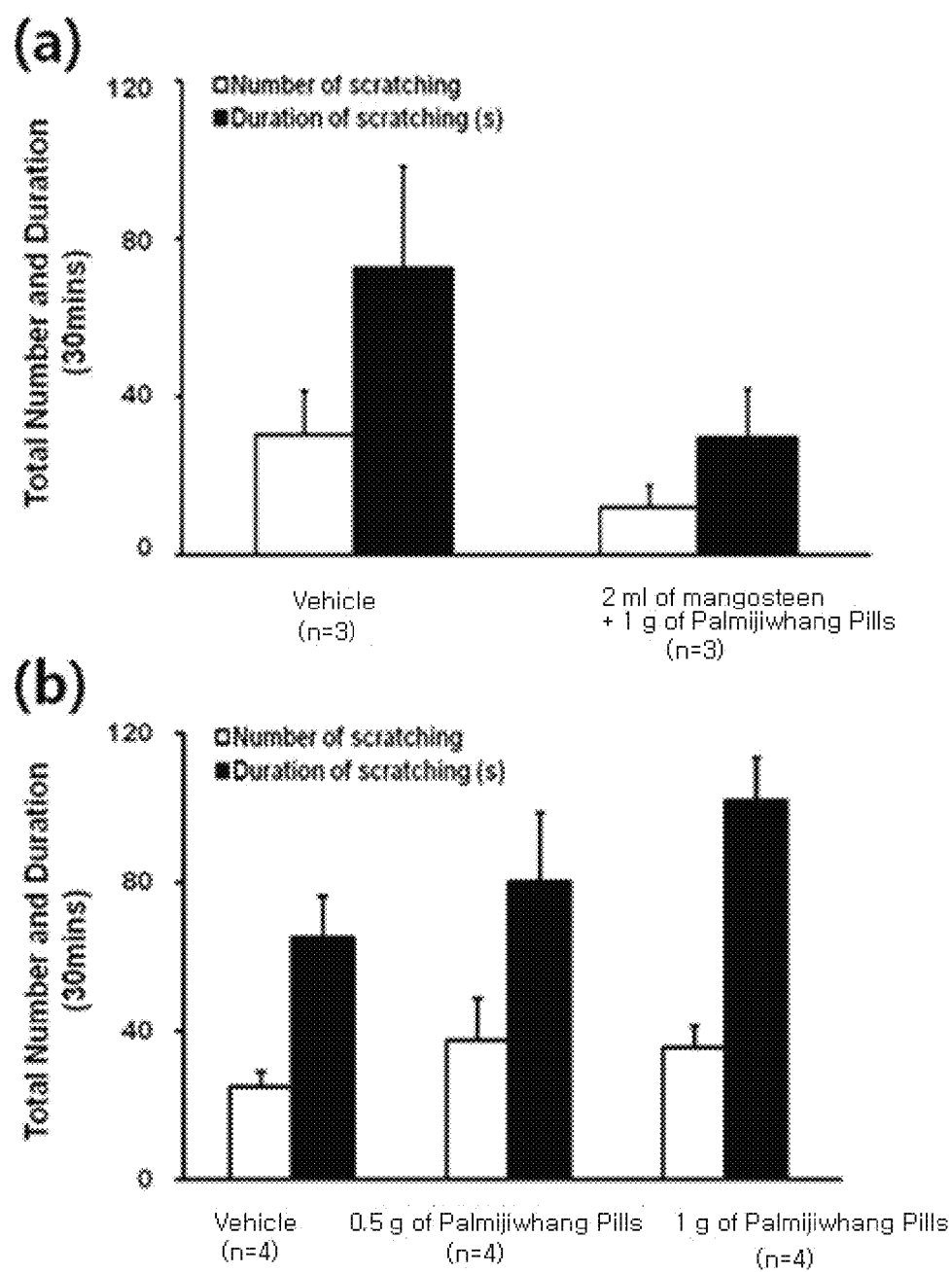
FIG. 6 shows a synergistic effect on itching relief caused by a combined treatment with "mangosteen" extract which is a natural substance acting as a selective 5HT2A antagonist, and "Palmijiwhang Pills (HMJG)" as a P2X antagonist on an itching model using rats (n=3 to 4).

In another embodiment of the present invention, itching animal models were treated with "mangosteen" extract as a natural substance acting as a 5-HT2 receptor antagonist, "Palmijiwhang Pills" as a natural substance acting as a P2X receptor antagonist in a combined manner. As a result, it is expressed that itching was remarkably relieved by synergistic effects of multi-targeting, as compared with a case that the mangosteen extract or the Palmijiwhang Pills is used respectively (FIG. 6).

Thus, the composition for treatment or prevention of the present invention may be used as a composition for treatment or prevention of pruritus or atopic dermatitis.

The embodiments of the present invention suggest that, as compared with respective treatments with the antagonists or the agonists according to the present invention, combined treatments with these components have excellent pain relieving effects and treating and preventing effects of pruritus or atopic dermatitis. This result suggests that, in the case of using an agonist or an antagonist simultaneously acting on two or more targets according to the present invention, it is possible to obtain the same relieving pain effects and treating and preventing effects of pruritus or atopic dermatitis.

The functional food composition of the present invention may include drugs, foods, beverages, and the like. Specifically, the functional food composition may include various foods, candies, chocolates, beverages, gum, tea, vitamin complexes, health supplement foods, etc., and may be used in the forms of powder, granules, tablets, capsules, or drinks. Further, the amount of the composition added to the food or beverage is not particularly limited but may be in a range of from 1 wt. % to 80 wt. % and preferably from 10 wt. % to 30 wt. % with respect to the total weight of the food, and may be in a range of 1 g to 10 g and preferably from 4 g to 8 g per 100 ml for a healthy drink.

In this case, the functional food composition may further include sitologically allowable food additives together with the composition of the present invention. For example, a liquid component used in a healthy drink containing the composition is not particularly limited, like other typical drinks, additional components such as flavoring agents or natural carbohydrates may be included. Examples of the natural carbohydrates include typical saccharides including monosaccharides such as glucose, or fructose; disaccharides such as maltose, or sucrose; polysaccharide such as dextrine, or cyclodextrin; and sugar alcohols such as xylitol, sorbitol, or erythritol. Further, examples of the flavoring agents include natural flavoring agents [thaumatin, stevia extract (for example, baudioside A, glycyrrhizin, etc.)] or synthetic flavoring agents (saccharin, aspartame, etc.). In this case, the amount of the natural carbohydrates may be in a range of from 1 g to 20 g, and preferably from 5 g to 12 g per 100 ml for a healthy drink composition.

Further, the functional food composition may include various nutritional supplements, vitamins, minerals (electrolytes), natural or synthetic flavoring agents, food colorants or inert fillers (cheese, chocolate, etc.), pectic acid or salt thereof, alginic acid or salt thereof, organic acid, protective colloid viscosity agents, pH controlling agents, stabilizers, preservatives, glycerin, alcohols or carbonating agents used for carbonated drinks, and may further include flesh for manufacturing natural fruit or vegetable beverages. In this case, the above mentioned components can be used alone or in combination thereof. Moreover, the amount of the additives is not particularly limited but may be selected in a range of from 1 wt. % to 50 wt. % with respect to the functional food.

The cosmetic composition in the present invention may additionally include pH controlling agents, fragrances, emulsifying agents, preservatives, etc. as necessary, so that it can be formulated into skin tonic, gel, water-soluble powder, fat-soluble powder, a water-soluble liquid, cream, or essence by typical cosmetic producing methods.

The cosmetic composition in the present invention can also be used as a dermatological composition for external application. An application agent containing the composition of the present invention as an active component can be produced in any form by typical producing methods. For example, when a cream-type application agent is produced, the natural composition of the present invention is added to a typical oil-in-water (O/W) or water-in-oil (W/O) cream base and fragrances, chelating agents, colorants, antioxidants, preservatives, etc. may be added thereto as necessary. Further, synthetic or natural substances such as proteins, minerals, vitamins, etc. may be used in combination thereof in order to improve properties. Such a dermatological composition for external application can be applied to a face and other body parts including a scalp, feet, etc.

Further, the cosmetic composition of the present invention may be formulated into skin gel, cream, lotion, powder, foundation, essence, gel, pack, foam cleansing, cleansing oil, powder foundation, emulsion foundation, or wax foundation. The cosmetic composition includes quasi-drugs such as soap, shampoo, conditioner, body lotion, body wash, toothpaste, oral spray, etc.

The components contained in the cosmetic composition of the present invention include the above mentioned components as active components and other components typically used for a cosmetic composition. For example, the components may additionally include one or more additives selected from a group consisting of vitamins, amino acids, proteins, surfactants, emulsifying agents, stabilizers, viscosity agents, preservatives, humectants, antioxidants, fragrances, colorants, tranquilizers and antioxidants.

As for the composition for treatment or prevention of the present invention, the antagonists or the agonists may be administered respectively and may be administered typically in a pharmaceutical mixture suitably formulated for a specific use or a desired purpose by being mixed with a diluting agent, a bonding agent, a slip modifier, a disintegrating agent, a coating substance, an emulsion, a suspension, a solvent, a stabilizer, a sorbefacient, and/or an ointment base. The mixture may be used for oral, injection or rectal administration, or external application.

An oral administering formulation may include, for example, tablets, coated tablets, dragees, hard or soft gelatin capsules, liquids, emulsions or suspensions. Administration may include: rectal administration, for example, using a suppository; local or transdermal administration, for example, in the form of ointment, cream, gel or liquid; or non-oral administration, for example, using an injection solution for systemic administration or spinal administration.

For manufacturing a tablet, coated tablet, dragee, or hard or soft gelatin capsule, the antagonist of the present invention may further be mixed with a pharmaceutically inert inorganic or organic excipient (or pharmaceutically acceptable carrier). Examples of the excipient suitable for manufacturing the tablet, coated tablet, dragee, hard or soft gelatin capsule, or the like may include lactose, maize starch or derivatives thereof, talc, stearic acid, or salts thereof. Examples of an excipient suitable for manufacturing the soft gelatin capsule may include a vegetable oil, wax, fat, semi-solid or liquid polyol. However, the soft gelatin capsule optionally does not need any excipient depending upon features of active ingredients. For manufacturing liquid and syrup products, the excipient useable herein may include, for example, water, polyol, sucrose, invert sugar and glucose. Examples of the excipient useable in manufacturing a solution for injection may include water, alcohol, polyol, glycerin and vegetable oil. Examples of the excipient useable in manufacturing locally or transdermally applicable formulations as well as suppositories may include natural oil or hardened oil, wax, fat and semi-solid or liquid polyol.

The composition of the present invention may further include a preservative, solvent, stabilizer, wetting agent, emulsifier, sweetener, colorant, aromatic, osmotic pressure controlling salt, buffer, coating agent, tension relieving agent, isotonic regulating agent or antioxidant, and may further include other therapeutically valuable medicaments.

Consequently, a pharmaceutical formulation for oral administration may include granulates, tablets, sugar coating tablets, capsules, pills, suspensions or emulsions, while a formulation for non-oral administration may include, for example, a formulation in a sterile solution for intravenous, intramuscular or subcutaneous administration, and may further include other substances, for example, salts or glucoses in order to prepare an isotonic solution. Alternatively, a suppository or pessary formulation may be administered, or other formulations for external use in any form of patch, lotion, solution, cream, ointment or dusting powder may also be adopted.

It should be understood that a proper dosage of the inventive composition may be determined according to different related parameters including, for example, formulation method, manner of administration, age, gender, body weight, condition of illness, food, administering time, administering route, excretory speed, and reaction sensibility, etc. Therefore, the dosage does not restrict the scope of the present invention in any way.

EXAMPLE

Hereinafter, the present invention will be described in detail by means of examples. However, the following examples are given for more concretely describing the present invention and may not be construed as a limitation of the scope of the present invention.

Particularly, in Examples, MDL 11,939 as a 5HT2A antagonist, ORG-25543 as a GlyT2 antagonist, RO-3 as a P2X antagonist, and glycine as a Glycine agonist were used and mangosteen extract, *gardeniae fructus* extract, *polygala tenuifolia* extract, Palmijiwhang Pills, and *Corni fructus* and *Alisma orientale* (Sam.) Juz. extracts as natural substances were used. It will be understood by those skilled in the art that, even in the case of using other compounds or natural substances, it is possible to obtain the same result.

Example 1

Determination of Pain Suppression Efficacy of Composite Composition in the Present Invention (1)

The present example was conducted to identify that a combined treatment using both of a 5HT2A antagonist (MDL 11,939) and a GlyT2 antagonist (ORG-25543) can induce synergistic effects with regard to analgesic efficacy expressed in a neuropathic pain rat model.

In order to prepare a neuropathic pain rat model (spinal nerve ligation (SNL) model), a male adult Sprague-Dawley rat was anaesthetized with isoflurane and its spinal nerves L5 were tied firmly (Kim and Chung, An experimental model for peripheral neuropathy produced by segmental spinal nerve ligation in the rat. Pain, 50: 355-363, 1992). One week later after surgical operation, MDL 11,939 and ORG-25543 were administered respectively or in combination thereof, and a pain relieving effect was monitored.

MDL 11,939 (Tocris Bioscience, USA) and ORG-25543 (CBvest inc, Korea) were dissolved in DMA/PG (2:8). MDL 11,939 was subcutaneously injected into the rat model and, immediately, ORG-25543 was subcutaneously injected into another part of the rat model. Then, 30 minutes and 60 minutes after administration, the extent of pain suppression was analyzed based on behaviors of the rat model.

The behavioral experiment was carried out with strict observance of clinical test procedures including criteria on randomization, a blind test, and use of a control group. By providing a mechanical stimulus to the left sole of the foot, a shrinking reaction to the stimulus was measured. This measurement value was determined by an up-down method using a von Frey monofilament (Baik et al., 2003 E. J. Baik, J. M. Chung and K. Chung, Peripheral norepinephrine exacerbates neuritis-induced hyperalgesia, J Pain 4 (2003), pp. 212-221; Chaplan et al., 1994 S. R. Chaplan, F. W. Bach, J. W. Pogrel, J. M. Chung and T. L. Yaksh, Quantitative assessment of tactile allodynia in the rat paw, J Neurosci Methods 53 (1994), pp. 55-63; Dixon, 1980 W. J. Dixon, Efficient analysis of experimental observations, Annu. Rev. Pharmacol. Toxicol. 20 (1980), pp. 441-462).

As a result shown in FIG. 1, it was found that synergistic effects by a combination of MDL 11,939 (2 or 5 mg/kg, s.c) as a 5HT2A antagonist and ORG-25543 (10 or 20 mg/kg, s.c.) as a GlyT2 antagonist is expressed in the neuropathic pain rat model. Although there was no effect in the case of using ORG-25543 of 10 or 20 mg/kg (the bottom in FIG. 1), when a small amount of ORG-25543 was combined with MDL 11,939, there was an analgesic efficacy to relieve physically abnormal pain derived by the neuropathic pain model in a dose-dependent manner (*$p<0.05$; **$p<0.01$; bar=mean) (the top in FIG. 1).

Example 2

Determination of Pain Suppression Efficacy of Composite Composition in the Present Invention (2)

The present example was conducted to identify that a combined treatment using a 5HT2A antagonist (MDL 11,939, Tocris Bioscience, USA) and a P2X3antagonist (RO-3, Tocris Bioscience, USA) can induce synergistic effects with regard to analgesic efficacy expressed in a formalin-derived pain model.

In order to prepare a pain model, a male Sprague-Dawley rat (230 to 260 g) was administered by intra plantar (i.pl) injection with formalin (about 35%, Samchun, Korea) diluted in a 5% saline solution. When formalin was administered into the foot of the rat, afferent nerves were stimulated in the beginning and then central sensitization of dorsal horn neurons reacted together. Therefore, the rat repeatedly swung or licked its foot administered with formalin. Such a behavior was monitored and a pain status was analyzed. The behavior monitoring was started 30 minutes before the administration of formalin, and 50 µl of formalin was administered into the left sole of the rat by using a 27-gauge needle (n=2 to 6). 10 minutes after administration, 2 mM of MDL 11,939 and 10 mM of RO-3 prepared by dissolving pain relieving components in 14% DSMO were administered to the rat respectively or in combination thereof. Then, a behavior of the rat was monitored for 60 minutes.

As a result shown in FIG. 2, it was found that the rat's pain is rapidly relieved by the combined administration of MDL 11,939 as a 5HT2A antagonist and RO-3 as a P2X3 antagonist, as compared with the single administration (*$p<0.05$; **$p<0.01$; bar=mean).

Example 3

Determination of Pain Suppression Efficacy of Composite Composition in the Present Invention (3)

In order to identify synergistic effects between multiple targets of the present invention from a natural composite composition, by using a combination of mangosteen as a 5HT2A antagonist, Palmijiwhang Pills as a P2X3 antagonist, and glycine as a glycine agonist, an experiment was carried out to confirm whether there was synergistic effects with regard to the analgesic efficacy in a neuropathic pain rat model (SNL), which is the same as that of Example 1, with a combined treatment of these components.

In the same manner as Example 1, a male adult Sprague-Dawley rat was anaesthetized with isoflurane and its spinal nerves L5 were tied firmly. One week later after surgical operation, mangosteen extract produced as described below, Palmijiwhang Pills and glycine were administered respectively or in combination thereof, and a pain relieving effect was monitored.

Data obtained in a case that the mixture of the three components was administered in a combined manner once or twice (twice with 15 minutes' intervals, and tests 30 minutes, 60 minutes, and 120 minutes after the last administration) (FIG. 3a) was compared with data obtained in a case that the mangosteen (50%/100%, 2.5 ml/animal) was administered alone (FIG. 3b) and data obtained in a case that the Palmijiwhang Pills (0.5 g/1 g/2 g) was administered alone (FIG. 3c). In each test, a gabapentin (GBP) group as a static control group of the SNL model was added so as to verify validity of the test.

Figure 3:
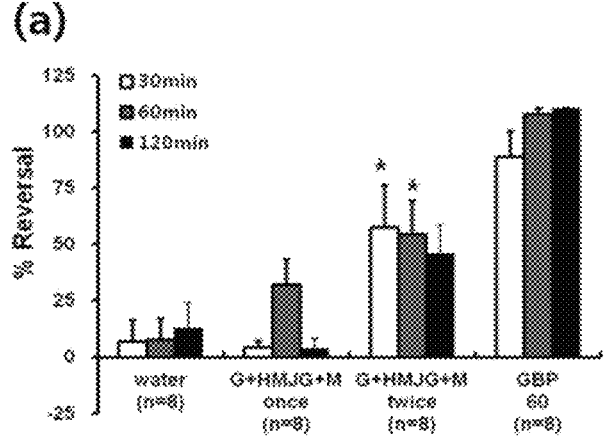
FIG. 3 shows a synergistic effect on pain control caused by a combined treatment with "mangosteen" extract which is a natural substance acting as a selective 5HT2A antagonist, a "Palmijiwhang Pills (HMJG)" as a P2X antagonist, and "glycine" as a glycine receptor agonist on a neuropathic pain rat model (SNL) (n=8, FIG. 3a). On the other hand, pain control efficacy was not observed in the case of a sole treatment with mangosteen (n=4, FIG. 3b) or a sole treatment with Palmijiwhang Pills (n=5, FIG. 3c). A result of each experiment was compared with a result of gabapentin (60 mpk, i.p.) as a positive control.
Figure 3:
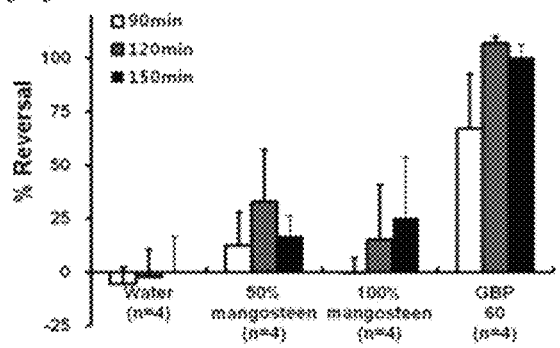
Figure 3:
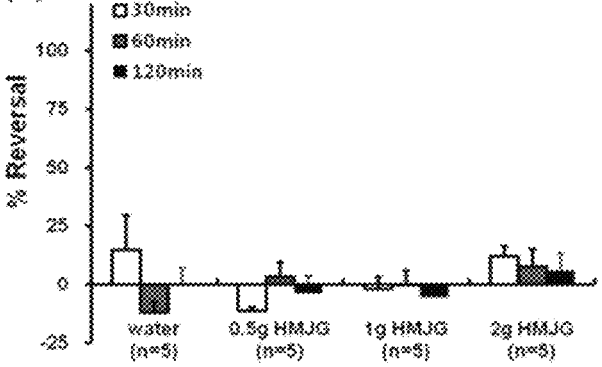

As a result shown in FIG. 3, when the mangosteen or the Palmijiwhang Pills was administered alone, a pain relieving effect was not significant, but when the three components were administered twice in a combined manner, a pain relieving effect was significantly increased (*p<0.05; bar=mean).

Mangosteen Extract Production Process 100 wt. % of dried powder of the mangosteen's flesh and pericarp was added to 99.9% ethanol and extracted twice at 50 to 60° C. for 3 hours. The extract was filtered with a filter having a pore size of 1 mm and concentrated to 1/10 of the original volume. Then, it was hot-air dried at 80 to 90° C. and ground by using a grinder for 100 mesh.

Example 4

Determination of Pain Suppression Efficacy of Composite Composition in the Present Invention (4)

In order to identify synergistic effects between multiple targets of the present invention from a natural composite composition, by using a combination of *gardeniae fructus*, *polygala tenuifolia*, or mangosteen as a 5HT2A antagonist, *Corni fructus/Alisma orientale* (Sam.) Juz. extracts as a P2X3 antagonist, and glycine as a glycine agonist, an experiment was carried out to confirm whether there was synergistic effects with regard to an analgesic efficacy in a neuropathic pain rat model (SNL), which is the same as that of Example 1, with a combined treatment of these components.

In the same manner as Example 1, a male adult Sprague-Dawley rat was anaesthetized with isoflurane and its spinal nerves L5 were tied firmly. One week later after surgical operation, one of *gardeniae fructus* extract (3.75 ml/10 ml/kg), *polygala tenuifolia* extract (2.81 ml/10 ml/kg) produced as described below, or mangosteen dried powder ((2 g/kg), *Corni fructus/Alisma orientale* (Sam.) Juz. mixed extract (2 ml/10 ml/kg), and glycine (2 g/kg) were repeatedly administered twice (twice with 15 minutes' intervals, and tests 30 minutes, 60 minutes, and 120 minutes after the last administration), and a pain relieving effect was monitored.

As a result shown in FIG. 4, it was found that when the three components were administered in a combined manner, there was a pain relieving effect.

*Gardenia fructus* Extract, *Polygala Tenuifolia* Extract, *Corni fructus/Alisma Orientale* (Sam.) Juz. Extract Production Process A dried herb medicine was put in a tenfold volume of distilled water and extracted twice at 50 to 60° C. for 3 hours. The extract was filtered with a filter having a pore size of 1 mm and concentrated to 1/10 of the original volume.

A mixture of dried herb medicines including 50 wt. % of *Corni fructus* and 50 wt. % of *Alisma orientale* (Sam.) Juz. was added to 70% ethanol and extracted twice at 50 to 60° C. for 3 hours. The extract was filtered with a filter having a pore size of 1 mm and concentrated to 1/10 of the original volume. Then, it was hot-air dried at 80 to 90° C. and ground by using a grinder for 100 mesh.

Example 5

Determination of Itching Relieving Effect of Composite Composition in the Present Invention (1)

An experiment was carried out to confirm whether there were synergistic effects with regard to itching relieving effect caused by a combined treatment with MDL 11,939 (Tocris Bioscience, USA) as a 5HT2A antagonist and RO-3 (Tocris Bioscience, USA) as a P2X3 antagonist on an itching model.

In order to prepare an itching model, serotonin hydrochloride, Sigma, H9523) at a concentration of 25 µg/µl was injected into a skin layer under a right shoulder blade of a male adult Sprague-Dawley rat. For 30 minutes after the injection of serotonin, a scratching behavior of the rat was monitored to check whether itching was induced.

MDL 11,939 and RO-3 were dissolved in DMA/PG (2:8) and subcutaneously injected into the rat model respectively or in combination thereof 30 minutes before the injection of serotonin, and an itching relieving effect was monitored.

As a result shown in FIG. 5, it was found that, as compared with a case that RO-3 as a P2X3 antagonist was administered to the itching model at a concentration of 3 mg/kg or a case that MDL 11,939 as a 5HT2A antagonist was administered to the itching model at a concentration of 0.5 mg/kg, when MDL 11,939 of 0.5 mg/kg and RO-3 of 3 mg/kg were administered in a combined manner, duration of scratching behavior was remarkably decreased, and, thus, itching was relieved.

Example 6

Determination of Itching Relieving Effect of Composite Composition in the Present Invention (2)

In order to identify synergistic effects between multiple targets of the present invention from a natural composite composition, by using a combination of mangosteen as a 5HT2A antagonist and Palmijiwhang Pills as a P2X3 antagonist, an experiment was carried out to confirm whether there was synergistic effects with regard to an itching relieving effect in an itching model, which is the same as that of Example 5, with a combined treatment of these components.

A mangosteen extract production method was the same as that of Example 3, and the itching model was prepared in the same manner as Example 5. It was observed that, as compared with the itching model supplied with tap water, when a mixture of mangosteen extract (100%, 2 ml/animal) and Palmijiwhang Pills (1 g) was administered to the itching model, whose itching was induced with serotonin, in a combined manner four times per day, itching was relieved (FIG. 6a). However, when the Palmijiwhang Pills (0.5, 1 g) was administered alone, itching did not tend to be relieved (FIG. 6b).

Although the present invention has been described in connection with the exemplary embodiments illustrated in the drawings, it is only illustrative. It will be understood by those skilled in the art that various modifications and equivalents can be made to the present invention. Therefore, the true technical scope of the present invention should be defined by the appended claims.

The invention claimed is:

1. A method for suppressing pain, comprising administering to a subject a composition comprising, as active components,
   (i) (a) a 5-hydroxytryptamine subtype 2 (5-HT2) receptor antagonist; and
   (ii) (b) a P2X receptor antagonist, (c) a glycine receptor agonist or a glycine transporter (GlyT) antagonist, or a mixture of (b) and (c),
   wherein (a) the 5-HT2 receptor antagonist is selected from the group consisting of MDL 11,939, mangosteen extract, and *Polygala tenuifolia* extract;
   (b) the P2X receptor antagonist is selected from the group consisting of Palmijiwhang Pills, and an extract of *Corni fructus* and *Alisma orientate* (Sam.) Juz; and
   (c) the glycine receptor agonist is glycine and the GlyT antagonist is ORG-25543;
   wherein the Palmijiwhang Pills are composed of extracts from the following eight herbs: *Rehmannia glutinosa, Cornus officinalis, Dioscorea batatas, Alisma orientale, Poria cocos, Paeonia suffruticosa, Cinnamomum cassia*, and *Aconitum carmichaeli*; and
   wherein when MDL 11,939 is the 5-HT2 receptor antagonist, MDL 11,939 is administered in an amount of from about 0.32 mg/kg to about 0.8 mg/kg;
   wherein when the mangosteen extract is the 5-HT2 receptor antagonist, the mangosteen extract is administered in an amount of from about 168 mg/kg to about 336 mg/kg;
   wherein when the *Polygala tenuifolia* extract is the 5-HT2 receptor antagonist, the *Polygala tenuifolia* extract is administered in an amount of about 118.4 mg/kg;
   wherein when the Palmijiwhang Pills are the P2X receptor antagonist, the Palmijiwhang Pills are administered in an amount of from about 240 mg/kg to about 960 mg/kg;
   wherein when the extract of *Corni fructus* and *Alisma orientate* (Sam.) Juz is the P2X receptor antagonist, the extract of *Corni fructus* and *Alisma orientate* (Sam.) Juz is administered in an amount of about 4.32 mg/kg of *Corni fructus* and of about 4.32 mg/kg of *Alisma orientate* (Sam.) Juz;
   wherein when glycine is the glycine receptor agonist, glycine is administered in an amount of about 320 mg/kg; and
   wherein when ORG-25543 is the GlyT antagonist, ORG-25543 is administered in an amount of from about 1.6 mg/kg to about 3.2 mg/kg.

2. The method of claim 1, in which the composition comprises (a) a 5-HT2 receptor antagonist and (c) a GlyT antagonist, wherein (a) the 5-HT2 receptor antagonist is MDL 11,939, and (c) the GlyT antagonist is ORG-25543.

3. The method of claim 1, in which the composition comprises (a) a 5-HT2 receptor antagonist, (b) a P2X receptor antagonist and (c) a glycine receptor agonist, wherein (a) the 5-HT2 receptor antagonist is mangosteen extract; (b) the P2X receptor antagonist is Palmijiwhang Pills; and (c) the glycine receptor agonist is glycine.

4. The method of claim 1, wherein the composition comprises (a) a 5-HT2 receptor antagonist, (b) a P2X receptor antagonist and (c) a glycine receptor agonist, wherein (a) the 5-HT2 receptor antagonist is mangosteen extract or *Polygala tenuifolia* extract; (b) the P2X receptor antagonist is an extract of *Corni fructus* and *Alisma orientale* (Sam.) Juz; and (c) the glycine receptor agonist is glycine.

* * * * *

UNITED STATES PATENT AND TRADEMARK OFFICE
CERTIFICATE OF CORRECTION

PATENT NO. : 9,526,718 B2
APPLICATION NO. : 14/128616
DATED : December 27, 2016
INVENTOR(S) : Doo Hyun Lee et al.

Page 1 of 1

It is certified that error appears in the above-identified patent and that said Letters Patent is hereby corrected as shown below:

In the Specification

Column 12, Line 23: "d1-tetrahydropalmatine," should be --dl-tetrahydropalmatine,--.

Column 12, Line 24: "1-coryclamine," should be --l-coryclamine,--.

Column 12, Line 25: "1-tetrahydrocoptisine," should be --l-tetrahydrocoptisine,--.

Column 12, Line 25: "d1-tetrahydrocoptisine," should be --dl-tetrahydrocoptisine,--.

Column 12, Lines 25-26: "1-isocorypalmine," should be --l-isocorypalmine,--.

Column 12, Line 27: "d1-tetrahydropalmatine" should be --dl-tetrahydropalmatine--.

Column 12, Line 29: "d1-tetrahydropalmatine" should be --dl-tetrahydropalmatine--.

Column 12, Line 37: "*fauriei* Brig." should be --*fauriei* Briq.--.

Column 12, Line 41: "*fauriei* Brig. Has" should be --*fauriei* Briq. has--.

In the Claims

Column 27, Line 15: "*Alisma orientate*" should be --*Alisma orientale*--.

Column 28, Lines 5-6: "*Alisma orientate*" should be --*Alisma orientale*--.

Column 28, Line 7: "*Alisma orientate*" should be --*Alisma orientale*--.

Column 28, Line 10: "*Alisma orientate*" should be --*Alisma orientale*--.

Signed and Sealed this
Eighteenth Day of April, 2017

Michelle K. Lee
*Director of the United States Patent and Trademark Office*